United States Patent
Harris et al.

(10) Patent No.: US 10,092,738 B2
(45) Date of Patent: Oct. 9, 2018

(54) METHODS AND DEVICES FOR INHIBITING NERVES WHEN ACTIVATING BROWN ADIPOSE TISSUE

(71) Applicant: Ethicon Endo-Surgery, Inc., Cincinnati, OH (US)

(72) Inventors: Jason L. Harris, Lebanon, OH (US); Tamara C. Baynham, Bowie, MD (US)

(73) Assignee: Ethicon LLC, Guaynabo, PR (US)

( * ) Notice: Subject to any disclaimer, the term of this patent is extended or adjusted under 35 U.S.C. 154(b) by 691 days.

(21) Appl. No.: 14/584,046

(22) Filed: Dec. 29, 2014

(65) Prior Publication Data

US 2016/0184568 A1  Jun. 30, 2016

(51) Int. Cl.
| | | |
|---|---|---|
| *A61M 1/30* | (2006.01) | |
| *A61M 37/00* | (2006.01) | |
| *A61N 1/04* | (2006.01) | |
| *A61N 5/06* | (2006.01) | |
| *A61M 35/00* | (2006.01) | |
| *A61F 7/00* | (2006.01) | |
| *A61N 1/36* | (2006.01) | |

(52) U.S. Cl.
CPC .............. *A61M 37/00* (2013.01); *A61F 7/00* (2013.01); *A61M 35/00* (2013.01); *A61N 1/0456* (2013.01); *A61N 1/0492* (2013.01); *A61N 1/36014* (2013.01); *A61N 1/36171* (2013.01); *A61N 5/0622* (2013.01)

(58) Field of Classification Search
CPC ......... A61M 37/00; A61M 35/00; A61F 7/00; A61N 1/0456
USPC .......................................................... 604/20
See application file for complete search history.

(56) References Cited

U.S. PATENT DOCUMENTS

| | | |
|---|---|---|
| 4,498,843 A | 2/1985 | Schneider et al. |
| 4,578,770 A | 3/1986 | Mitani |
| 4,596,792 A | 6/1986 | Vyas |
| 4,599,230 A | 7/1986 | Milich et al. |

(Continued)

FOREIGN PATENT DOCUMENTS

| | | |
|---|---|---|
| CN | 2045308 | 10/1989 |
| CN | 2045380 U | 10/1989 |

(Continued)

OTHER PUBLICATIONS

"3M CoTran™ 9702 Membrane" Brochure. (2009).

(Continued)

*Primary Examiner* — Phillip Gray
(74) *Attorney, Agent, or Firm* — Mintz Levin Cohn Ferris Glovsky and Popeo, P.C.

(57) ABSTRACT

Methods and devices are provided for inhibiting nerves when activating brown adipose tissue (BAT). In general, a first nerve type (e.g., sympathetic nerves) innervating BAT can be activated while at least one other nerve type (e.g., parasympathetic nerves and/or sensory nerves) innervating BAT is being suppressed. A first neuromodulator (e.g., an electrical signal, a chemical, a light, cooling, etc.) can be applied to activate the first nerve type, and a second neuromodulator can be applied to inhibit the at least one other nerve type. In this way, parasympathetic nerves and/or sensory nerves innervating BAT can be inhibited when activating sympathetic nerves innervating BAT.

21 Claims, 4 Drawing Sheets

(56) References Cited

U.S. PATENT DOCUMENTS

| | | |
|---|---|---|
| 4,599,231 A | 7/1986 | Milich et al. |
| 4,601,903 A | 7/1986 | Frasch |
| 4,608,251 A | 8/1986 | Mia |
| 4,772,631 A | 9/1988 | Holloway et al. |
| 4,927,836 A | 5/1990 | Holloway et al. |
| 4,937,267 A | 6/1990 | Holloway et al. |
| 4,978,338 A | 12/1990 | Melsky et al. |
| 5,434,184 A | 7/1995 | Holloway et al. |
| 5,453,270 A | 9/1995 | Bills |
| 5,486,359 A | 1/1996 | Caplan et al. |
| 5,724,996 A | 3/1998 | Piunti |
| 5,731,408 A | 3/1998 | Hadley et al. |
| 5,736,396 A | 4/1998 | Bruder et al. |
| 5,789,654 A | 8/1998 | Lowell et al. |
| 5,811,094 A | 9/1998 | Caplan et al. |
| 5,827,735 A | 10/1998 | Young et al. |
| 5,827,740 A | 10/1998 | Pittenger |
| 5,837,539 A | 11/1998 | Caplan et al. |
| 5,837,670 A | 11/1998 | Hartshorn |
| 5,843,723 A | 12/1998 | Dubensky, Jr. et al. |
| 5,911,992 A | 6/1999 | Braswell et al. |
| 6,069,147 A | 5/2000 | Williams et al. |
| 6,071,747 A | 6/2000 | Strosberg et al. |
| 6,072,100 A | 6/2000 | Mooney et al. |
| 6,197,580 B1 | 3/2001 | Susulic et al. |
| 6,207,878 B1 | 3/2001 | Campbell et al. |
| 6,224,873 B1 | 5/2001 | Jones |
| 6,246,912 B1 | 6/2001 | Sluijter et al. |
| 6,381,496 B1 | 4/2002 | Meadows et al. |
| 6,445,955 B1 | 9/2002 | Michelson et al. |
| 6,451,336 B2 | 9/2002 | Sugano et al. |
| 6,475,530 B1 | 11/2002 | Kuhrts |
| 6,532,286 B1 | 3/2003 | Burg |
| 6,532,386 B2 | 3/2003 | Sun et al. |
| 6,565,847 B1 | 5/2003 | Gorsek |
| 6,602,694 B1 | 8/2003 | Albrandt et al. |
| 6,605,297 B2 | 8/2003 | Nadachi et al. |
| 6,620,594 B1 | 9/2003 | Giacobino et al. |
| 6,645,229 B2 | 11/2003 | Matsumura et al. |
| 6,694,185 B2 | 2/2004 | Orton |
| 6,908,987 B2 | 6/2005 | Spiegelman et al. |
| 6,922,590 B1 | 7/2005 | Whitehurst |
| 6,927,288 B2 | 8/2005 | Ito |
| 6,983,753 B1 | 1/2006 | Lenhard et al. |
| 7,060,437 B1 | 6/2006 | Kopchick |
| 7,091,006 B2 | 8/2006 | Spiegelman et al. |
| 7,135,611 B2 | 11/2006 | MacDougald et al. |
| 7,191,007 B2 | 3/2007 | Desai et al. |
| 7,250,283 B2 | 7/2007 | Spiegelman et al. |
| 7,264,602 B1 | 9/2007 | Longsworth |
| 7,300,409 B2 | 11/2007 | Kopanic, Jr. et al. |
| 7,367,341 B2 | 5/2008 | Anderson et al. |
| 7,396,642 B2 | 7/2008 | Yamaoka et al. |
| 7,440,806 B1 | 10/2008 | Whitehurst et al. |
| 7,476,406 B1 | 1/2009 | Smidt |
| 7,526,061 B2 | 4/2009 | Kobayashi |
| 7,576,052 B2 | 8/2009 | Kahn et al. |
| 7,599,736 B2 | 10/2009 | DiLorenzo |
| 7,599,743 B2 | 10/2009 | Hassler, Jr. et al. |
| 7,599,744 B2 | 10/2009 | Giordano et al. |
| 7,647,112 B2 | 1/2010 | Tracey et al. |
| 7,818,060 B2 | 10/2010 | Torgerson |
| 7,935,073 B2 | 5/2011 | Levine et al. |
| 7,979,137 B2 | 7/2011 | Tracey et al. |
| 8,126,530 B2 | 2/2012 | Bare et al. |
| 8,162,530 B2 | 4/2012 | Lee |
| 8,476,227 B2 | 7/2013 | Kaplan et al. |
| 8,690,934 B2 | 4/2014 | Boyden et al. |
| 8,696,616 B2 | 4/2014 | Baynham et al. |
| 8,812,100 B2 | 8/2014 | Voegele et al. |
| 8,911,701 B2 | 12/2014 | Gaillard et al. |
| 9,044,606 B2 | 6/2015 | Harris et al. |
| 9,662,486 B2 | 5/2017 | Harris et al. |
| 2001/0014815 A1 | 8/2001 | Matsumura et al. |
| 2001/0032337 A1 | 10/2001 | Forman |
| 2002/0016618 A1 | 2/2002 | DaSilva et al. |
| 2002/0123774 A1 | 9/2002 | Loeb et al. |
| 2002/0165586 A1 | 11/2002 | Hill et al. |
| 2003/0082168 A1 | 5/2003 | Yegorova |
| 2003/0104081 A1 | 6/2003 | Rombi |
| 2003/0119775 A1 | 6/2003 | Surwit et al. |
| 2003/0181958 A1 | 9/2003 | Dobak, III |
| 2003/0212016 A1 | 11/2003 | Gimeno et al. |
| 2003/0220238 A1 | 11/2003 | Adams et al. |
| 2004/0039312 A1 | 2/2004 | Hillstead et al. |
| 2004/0077556 A1 | 4/2004 | Chinery |
| 2005/0043524 A1 | 2/2005 | Bhanot et al. |
| 2005/0045498 A1 | 3/2005 | Purcell et al. |
| 2005/0080026 A1 | 4/2005 | Steuernagel et al. |
| 2005/0136429 A1 | 6/2005 | Guarente et al. |
| 2005/0177067 A1 | 8/2005 | Tracey et al. |
| 2005/0261223 A1 | 11/2005 | Czech et al. |
| 2005/0277998 A1 | 12/2005 | Tracey et al. |
| 2005/0288740 A1 | 12/2005 | Hassler et al. |
| 2006/0004421 A1 | 1/2006 | Bennett et al. |
| 2006/0008540 A1 | 1/2006 | Xiu |
| 2006/0014178 A1 | 1/2006 | Whitson et al. |
| 2006/0084637 A1 | 4/2006 | Alemany |
| 2006/0121158 A1 | 6/2006 | Ferruzzi et al. |
| 2006/0190053 A1 | 8/2006 | Dobak, III |
| 2006/0195145 A1 | 8/2006 | Lee et al. |
| 2006/0195146 A1 | 8/2006 | Tracey et al. |
| 2006/0195153 A1 | 8/2006 | DiUbaldi et al. |
| 2006/0204599 A1 | 9/2006 | Wheat |
| 2006/0223104 A1 | 10/2006 | Kahn et al. |
| 2007/0055154 A1 | 3/2007 | Torbati |
| 2007/0162085 A1 | 7/2007 | DiLorenzo |
| 2007/0185541 A1 | 8/2007 | DiUbaldi et al. |
| 2007/0282318 A1 | 12/2007 | Spooner et al. |
| 2008/0046012 A1 | 2/2008 | Covalin et al. |
| 2008/0080026 A1 | 4/2008 | Mestha et al. |
| 2008/0132962 A1 | 6/2008 | DiUbaldi et al. |
| 2008/0138449 A1 | 6/2008 | Heuer et al. |
| 2008/0139875 A1 | 6/2008 | Tracey et al. |
| 2008/0147146 A1 | 6/2008 | Wahlgren et al. |
| 2008/0262411 A1 | 10/2008 | Dobak |
| 2008/0293830 A1 | 11/2008 | Katagiri et al. |
| 2009/0012555 A1 | 1/2009 | Makower et al. |
| 2009/0018594 A1 | 1/2009 | Laufer et al. |
| 2009/0024144 A1 | 1/2009 | Zeiner et al. |
| 2009/0024192 A1 | 1/2009 | Mulholland et al. |
| 2009/0054487 A1 | 2/2009 | Kolonics et al. |
| 2009/0062193 A1 | 3/2009 | Weyer et al. |
| 2009/0081715 A1 | 3/2009 | Burns-Guydish et al. |
| 2009/0082641 A1 | 3/2009 | Giftakis et al. |
| 2009/0093858 A1 | 4/2009 | DiUbaldi |
| 2009/0118780 A1 | 5/2009 | DiLorenzo |
| 2009/0132018 A1 | 5/2009 | DiUbaldi et al. |
| 2009/0149918 A1 | 6/2009 | Krulevitch et al. |
| 2009/0157149 A1 | 6/2009 | Wahlgren et al. |
| 2009/0171375 A1 | 7/2009 | Coe et al. |
| 2009/0202387 A1 | 8/2009 | Dlugos, Jr. et al. |
| 2009/0202659 A1 | 8/2009 | Gimble |
| 2009/0204131 A1 | 8/2009 | Ortiz et al. |
| 2009/0228078 A1 | 9/2009 | Zhang et al. |
| 2009/0306739 A1 | 12/2009 | DiLorenzo |
| 2010/0056433 A1 | 3/2010 | Sensfuss |
| 2010/0056948 A1 | 3/2010 | Hornby et al. |
| 2010/0161001 A1 | 6/2010 | DiUbaldi et al. |
| 2010/0161005 A1 | 6/2010 | Wahlgren et al. |
| 2010/0222734 A1 | 9/2010 | Jayes et al. |
| 2010/0239648 A1 | 9/2010 | Smith et al. |
| 2010/0249677 A1 | 9/2010 | DiUbaldi et al. |
| 2010/0312295 A1 | 12/2010 | Vase et al. |
| 2011/0094773 A1 | 4/2011 | Bare et al. |
| 2011/0144490 A1 | 6/2011 | Davis et al. |
| 2011/0152987 A1 | 6/2011 | Wahlgren et al. |
| 2011/0237922 A1 | 9/2011 | Parker, III et al. |
| 2011/0263490 A1 | 10/2011 | Kaplan et al. |
| 2011/0270360 A1 | 11/2011 | Harris et al. |
| 2012/0165792 A1 | 6/2012 | Ortiz et al. |
| 2012/0172783 A1 | 7/2012 | Harris et al. |
| 2012/0290023 A1* | 11/2012 | Boyden .......... A61N 5/025 607/3 |

(56) References Cited

U.S. PATENT DOCUMENTS

| | | | |
|---|---|---|---|
| 2013/0110220 A1 | 5/2013 | Brown | |
| 2014/0018767 A1 | 1/2014 | Harris et al. | |
| 2014/0088487 A1 | 3/2014 | Harris et al. | |
| 2014/0199278 A1 | 7/2014 | Kaplan et al. | |
| 2015/0258326 A1 | 9/2015 | Aronhal et al. | |

FOREIGN PATENT DOCUMENTS

| | | | |
|---|---|---|---|
| CN | 2520883 | Y | 11/2002 |
| CN | 2899835 | Y | 5/2007 |
| EP | 1060728 | A1 | 12/2000 |
| EP | 1172113 | A1 | 1/2002 |
| JP | 2001259047 | A | 9/2001 |
| JP | 2005021940 | A | 1/2005 |
| JP | 2013-126486 | | 6/2013 |
| WO | WO-1989011701 | A1 | 11/1989 |
| WO | WO-1991000730 | A1 | 1/1991 |
| WO | WO-199322277 | A1 | 11/1993 |
| WO | WO-199506411 | A1 | 3/1995 |
| WO | WO-199814200 | A1 | 4/1998 |
| WO | WO-199845313 | A1 | 10/1998 |
| WO | WO-199856397 | A1 | 12/1998 |
| WO | WO-199900123 | A1 | 1/1999 |
| WO | WO-200155109 | A1 | 8/2001 |
| WO | WO-200170337 | A1 | 9/2001 |
| WO | WO-200170708 | A1 | 9/2001 |
| WO | WO-200215909 | A1 | 2/2002 |
| WO | WO-2002012887 | A2 | 2/2002 |
| WO | WO-2002018327 | A2 | 3/2002 |
| WO | WO-2002059095 | A1 | 8/2002 |
| WO | WO-2002059107 | A1 | 8/2002 |
| WO | WO-2002059108 | A1 | 8/2002 |
| WO | WO-2002059117 | A1 | 8/2002 |
| WO | WO-2002067869 | A2 | 9/2002 |
| WO | WO-2002068387 | A2 | 9/2002 |
| WO | WO-2002068388 | A2 | 9/2002 |
| WO | WO-2002081443 | A1 | 10/2002 |
| WO | WO-2002085925 | A2 | 10/2002 |
| WO | WO-2003006620 | A2 | 1/2003 |
| WO | WO-2003007949 | A1 | 1/2003 |
| WO | WO-2003009847 | A1 | 2/2003 |
| WO | WO-2003009850 | A1 | 2/2003 |
| WO | WO-2003026576 | A2 | 4/2003 |
| WO | WO-2004078716 | A1 | 9/2004 |
| WO | WO-2004078717 | A1 | 9/2004 |
| WO | WO-2004087159 | A1 | 10/2004 |
| WO | WO-2005033254 | A1 | 4/2005 |
| WO | WO-2005040109 | A1 | 5/2005 |
| WO | WO-2005047251 | A1 | 5/2005 |
| WO | WO-2005077935 | A1 | 8/2005 |
| WO | WO-2006019787 | A2 | 2/2006 |
| WO | WO-2006020277 | A2 | 2/2006 |
| WO | WO-2006072393 | A2 | 7/2006 |
| WO | WO-2007015157 | A2 | 2/2007 |
| WO | WO-2007015162 | A1 | 2/2007 |
| WO | WO-2007041052 | A2 | 4/2007 |
| WO | WO-2007041061 | A2 | 4/2007 |
| WO | WO-2007047496 | A2 | 4/2007 |
| WO | WO-2008063330 | A2 | 5/2008 |
| WO | WO-2008087190 | A2 | 7/2008 |
| WO | WO-2009008991 | A2 | 1/2009 |
| WO | WO-2009067501 | A2 | 5/2009 |
| WO | WO-2009097542 | A2 | 8/2009 |
| WO | WO-2009117415 | A2 | 9/2009 |
| WO | WO-2013115756 | A2 | 8/2013 |

OTHER PUBLICATIONS

"3M CoTran™ 9705 Membrane" Brochure. (2009).
"3M CoTran™ 9706 Membrane" Brochure. (2009).
"3M CoTran™ 9707 Membrane" Brochure. (2009).
"3M CoTran™ 9712 Membrane" Brochure. (2009).
"3M CoTran™ 9715 Membrane" Brochure. (2009).
"3M CoTran™ 9716 Membrane" Brochure. (2009).
"3M CoTran™ 9728 Membrane" Brochure. (2009).
"3M CoTran™ Membranes" Brochure. (2010).
"Cell Junctions, Cell Adhesions, and the Extracellular Matrix." *Molecular Biology of the Cell*. Alberts et al., eds. New York: Garland Publishing. Chapter 19(1994):949-1009.
"Shining a Light on Disease—Tracking Light-Emitting Bacteria During Infection." *Soc. Gen. Microbiol*. (2009).
Accornero et al. "Selective Activation of Peropheral Nerve Fibre Groups of Different Diameter by Triangular Shaped Simulus Pulses." *J. Physiol*. 273(1977):539-560.
*Adenovirus Methods and Protocols*. Wold, ed. New Jersey: Humana Press. (1998).
Ausubel et al. "Preparation of a Specific Retrovirus Producer Cell Line." *Current Protocols in Molecular Biology*. New York: Wiley & Sons. (1989):9.10-9.14.
Bakshi et al. "1-Amino-1,2,3,4-tetrahydronaphthalene-2-carboxylic Acid as a Tic Mimetics: Application in the Synthesis of Potent Human Melanocortin-4 Receptor Selective Agonists." *Bioorg. Med. Chem. Lett*. 15.14(2005):3430-3433.
Bartelet et al. "Brown Adipose Tissue Activity Controls Trigylceride Clearance." *Nat. Med*. 17.2(2011):200-206.
Bartelet et al. "The Holy Grail of Metabolic Disease: Brown Adipose Tissue." *Curr. Opin. Lipidol*. 23.3(2012)190-195.
Bartness et al. "Brain-Adipose Tissue Neural Crosstalk." *Physiol. Behav*. 91.4(2007):343-351.
Bartness et al. "Sympathetic and Sensory Innervation of Brown Adipose Tissue." *Int. J. Obes*. (*Lond*). 34(2010):536-542.
Bartness et al. "Sympathetic and Sensory Innervation of White Adipose Tissue." *J. Lipid Res*. 48(2007):1655-1672.
*Basic Methods in Molecular Biology*. Davis et al., eds. New York: Elsevier. (1986).
Berkner. "Development of Adenovirus Vectors for the Expression of Heterologous Genes." *Biotechniques*. 6.7(1988):616-629.
Bing et al. "Hyperphagia in Cold-Exposed Rats is Accompanied by Decreased Plasma Leptin but Unchanged Hypothamalic NPY."*Am. J. Physiol. Regul. Integ. Comp. Physiol*. 274(1998):62-68.
Boshart et al. "A Very Strong Enhancer is Located Upstream of an Immediate Early Gene of Human Cytomegalovirus." *Cell*. 41.2(1985):521-530.
Bostock et al. "Velocity Recovery Cycles of C Fibres Innervating Human Skin." *J. Physiol*. 553.2(2003):649-663.
Bouillaud et al. "Increased Level of mRNA for the Uncoupling Protein in Brown Adipose Tissue of Rats during Thermogenesis Induced by Cold Exposure or Norepinephrine Infusion." *J. Biol. Chem*. 259.18(1984):11583-11586.
Capecchi. "High Efficiency Transformation by Direct Microinjection of DNA into Cultured Mammalian Cells." *Cell*. 22(1980):479-488.
Cassiede et al. "Osteochondrogenic Potential of Marrow Mesenchymal Progenitor Cells Exposed to TGF-β 1 or PDGF-BB as Assayed In Vivo and In Vitro." *J. Bone Miner. Res*. 11.9(1996):1264-1273.
Cheneval et al. "Cell-Free Transcription Directed b the 422 Adipose P2 Gene Promoter: Activation by the CCAAT/Enhancer Binding Protein." *PNAS*. 88.19(1991):8465-8469.
Chu et al. "SV40 DNA Transfection of Cells in Suspension: Analysis of Efficiency of Transcription and Translation of T-Antigen." *Gene*. 13.2(1981):197-202.
Clark et al. "Gene Transfer into the CNS Using Recombinant Adeno-Associated Virus: Analysis of Vector DNA Forms Resulting in Sustained Expression." *J. Drug Target*. 7.4(1999):269-283.
Collins. "The Cervical Sympathetic Nerves in Surgery of the Neck." *Otolaryngol Head Neck Surg*. 105(1991):544-555.
Crago et al. "The Choice of Pulse Duration for Chronic Electrical Stimulation via Surface, Nerve, and Intramuscular Electrodes." *Ann. Biomed. Eng*. 2(1974):252-264.
Davidson et al. "A Model System for in vivo Gene Transfer into the Central Nervous System Using an Adenoviral Vector." *Nat. Genet*. 3.3(1993):219-223.
Douglas et al. "A System for the Propagaton of Adenoviral Vectors with Genetically Modified Receptor Specificities." *Nat. Biotechnol*. 17.5(1999):470-475.
Drazen et al. "Peripheral Signals in the Control of Satiety and Hunger." *Curr. Opin. Clin. Nutr. Metab. Care*. 6.6(2003):621-629.

(56) References Cited

OTHER PUBLICATIONS

Dull et al. "A Third-Generation Lentivirus Vector with a Conditional Packaging System." *J. Virol.* 72.11(1998):8463-8471.
Ekblom et al. "Laminin Isoforms and Epithelial Development." *Ann. N.Y. Acad. Sci.* 857(1998):194-211.
Enerback. "The Origins of Brown Adipose Tissue." *New Eng. J. Med.* 360.19(2009):2021-2023.
Feigner et al. "Lipofection: A Highly Efficient, Lipid-Mediated DNA-Transfection Procedure." *PNAS.* 84.21(1987):7413-7417.
Flaim et al. "Functional and Anatomical Characteristics of the Nerve-Brown Adipose Interation in the Rat." *Pflügers Arch.* 365(1976):9-14.
Foster et al. "Hetergeneity of the Sympathetic Innervation of Rat Interscapular Browrn Adipose Tissue via Intercostal Nerves." *Can. J. Physiol. Pharmacol.* 60.6(1982):747-754.
Frolov et al. "Alphavirus-Based Expression Vectors: Strategies and Applications." *PNAS.* 93.21(1996):11371-11377.
Fruhbeck et al. "BAT: A New Target for Human Obesity?" *Trends Pharmacol. Sci.* 30.8(2009):387-396.
Giordano et al. "Presence and Distribution of Cholinergic Nerves in Rat Mediastinal Brown Adipose Tissue." *J. Histochem. Cytochem.* 52.7(2004):923-930.
Graham et al. "A New Technique for the Assay of Infectivity of Human Adenovirus 5 DNA." *Virology.* 52.2(1973):456-467.
Grill et al. "Effect of Stimulus Pulse Duration on Selectivity of Neural Stimulation." *IEEE Trans. Biomed. Eng.* 43.2(1996):161-166.
Grill et al. "Stimulus Waveforms for Selective Neural Stimulation." *IEEE Eng. Med. Biol.* (1995):375-385.
Gronthos et al. "The STRO-1+ Fraction of Adult Human Bone Marrow Contains the Osteogenic Precursors." *Blood.* 84.12(1994):4164-4173.
Heaton. "The Distribution of Brown Adipose Tissue in the Human." *J. Anat.* 112(1972):35-39.
Herlitze et al. "New Optical Tools for Controlling Neuronal Activity." *Curr. Opin. Neurobiol.* 17.1(2007):87-94.
Herpin et al. "Discovery of Tyrosine-Based Potent and Selective Melanocortin-1 Receptor Small-Molecule Agonists with Anti-Inflammatory Properties." *J. Med. Chem.* 46.7(2003):1123-1126.
Himms-Hagen et al. "Brown Adipose Tissue Thermogenesis: Interdisciplinary Studies." *FASEB J.* 4(1990):2894-2898.
Hodgkin et al. "A Quantitative Description of Membrane Current and its Application to Conduction and Excitation in Nerve." *J. Physiol.* 117(1952):500-544.
Horwitz et al. "Norepinephrine-Induced Depolarization of Brown Fat Cells." *PNAS.* 64(1969):113-120.
Jaiswal et al. "Osteogenic Differentiation of Purified, Culture-Expanded Human Mesenchymal Stem Cells In Vitro." *J. Cell. Biochem.* 64.2(1997):295-312.
Johnstone et al. "In Vitro Chondrogenesis of Bone Marrow-Derived Mesenchymal Progenitor Cells." *Exp. Cell. Res.* 238.1(1998):265-272.
Kafri et al. "A Packaging Cell Line for Lentivirus Vectors." *J. Virol.* 73.1(1999):576-584.
Klein et al. "High-Velocity Microprojectiles for Delivering Nucleic Acids into Living Cells." *Nature.* 327(19897):70-73.
Ladner et al. "Human CSF-1: Gene Structure and Alternative Splicing of mRNA Precursors." *EMBO J.* 6.9(1987):2693-2698.
Lever et al. "Demonstration of a Catecholaminergic Innervation in Human Perirenal Brown Adipose Tissue at Various Ages in the Adult." *Anat. Rec.* 215.3(1986):251-5, 227-229.
Lin et al. "Spatially Discrete, Light Driven Protein Expression." *Chem. Biol.* 9(2002)1 347-1353.
Makino et al. "Cardiomyocytes can be Generated from Marrow Stromal Cells in vitro." *J. Clin. Invest.* 103.5(1999):697-705.
Mannino et al. "Liposome Mediated Gene Transfer." *Biotech.* 6.7(1988):682-690.

Masamoto et al. "Intragastric Administration of TRPV1, TRPV3, TRPM8, and TRPA1 Agonists Modulates Autonomic Thermoregulation in Different Manners in Mice." *Biosci. Biotechnol. Biochem.* 73.5(2009):1021-127.
Mayer et al. "Biologically Active Molecules with a 'Light Switch.'" *Angew. Chem. Int. Ed.* 45(2006):4900-4921.
McKnight et al. "The Distral Transcription Signals of the Herpesvirus tk Gene Share a Common Hexanucleotide Control Sequence." *Cell.* 37.1(1984):253-262.
McMinn et al. "Neuroendocrine Mechanisms Regulating Food Intake and Body Weight." *Obes. Rev.* 1.1(2000):37-46.
Minokoshi et al. "Sympathetic Acticaction of Lipid Synthesis in Brown Adipose Tissue in the Rat." *J. Physiol.* 398(1988):361-370.
Mochizuki et al. "High-Titer Human Immunodeficiency Virus Type 1-Based Vector Systems for Gene Delivery into Nondividing Cells." *J. Virol.* 72.11(1998):8873-8883.
*Molecular Cloning.* Sambrook et al., eds.New York: Cold Spring Harbor Laboratories. (1989).
Morrison et al. "Central Control of Brown Adipose Tissue Thermogenesis." *Front. Endocrinol.* 3(2012):1-19.
Morrison et al. "Central Neural Pathways for Thermoregulation." *Front Biosci.* 16(2011):74-104.
National Institute of Health. "Clinical Guidelines on the Idenfication, Evaluation, and Treatment of Overweight and Obesity in Adults." (1998).
Ng et al. "Evolution of the Functional Human β-Actin Gene and its Multi-Pseudogene Family: Conservation of Noncoding Regions and Chromosomal Dispersion of Pseudogenes." *Mol. Cell Biol.* 5.10(1985):2720-2732.
Palucki et al. "Discovery of (2 S)-N-[(1 R)-2-[4-cyclohexyl-4-[[(1,1-dimethylethyl)amino]carbonyl]-1-piperidinyl]-1-[(4-fluorophenyl)methyl]-2-oxoethyl]-4-methyl-2-piperazinecarboxamide (MB243), a Potent and Selective Melanocortin Subtype-4 Receptor Agonist." *Bioorg. Med. Chem. Lett.* 15.1(2005):171-175.
Rehnmark et al. "α- and β-Adrenergic Induction of the Expression of the Uncoupling Protein Thermogenin in Brown Adipocytes Differentiated in Culture." *J. Biol. Chem.* 265(1990):16464-16471.
Reiman et al. "Characterization and Functional Role of Voltage Gated Cation Conductances in the Glucagon-Like Peptide-1 Secreting GLUTag Cell Line." *J. Physiol.* 563(2005):161-171.
Rial et al. "The Structure and Function of the Brown Fat Uncoupling UCP1: Current Status." *Biofactors.* 8(1998):209-219.
Ricquier et al. "Contribution to the Identification and Analysis of the Mitochondrial Uncoupling Proteins." *J. Bioengergetics Biomembranes.* 31.5(1999):407-418.
Rosell et al. "Skin Impedance from 1 Hz to 1 MHz." *IEEE Trans. Biomed. Eng.* 35.8(1988):649-651.
Rosenfeld et al. "Adenovirus-Mediated Transfer of Recombinant α 1-Antitrypsin Gene to the Lung Epithelium in vivo." *Science.* 252(1991):431-434.
Rosenfeld et al. "In Vivo Transfer of the Human Cystic Fibrosis Transmembrane Conductance Regulator Gene to the Airway Epithelium." *Cell.* 68.1(1992):143-155.
Rothwell et al. "A Role for Brown Adipose Tissues in Diet-Induced Thermogenesis." *Nature.* 281(1979):31-35.
Saito et al. "High Incidence of Metabolically Active Brown Adipose Tissue in Healthy Adult Humans: Effects of Cold Exposure and Adisposity." *Diabetes.* 58(2009):1526-1531.
Salmons et al. "Targeting of Retroviral Vectors for Gene Therapy." *Hum. Gene Ther.* 4(1993):129-141.
Schmelz et al. "Delayed Responses to Electrical Stimuli Reflect C-Fiber Responsiveness in Human Microneurography." *Exp. Brain Res.* 104(1995):331-336.
Sebhat et al. "Design and pharmacology of N-[(3R)-1,2,3,4-tetrahydroisoquinolinium-3-ylcarbonyl]-(1R)-1-(4-chlorobenzyl)-2[4-cyclohexyl-4-(1H-1,2,4-triazol-1-ylrnethyl)piperidin-1-yl]-2-oxoethylamine (1), a potent, selective, melanocortin subtype-4 receptor agonist." *J. Med. Chem.* 45.21(2002):4589-4593.
Seydoux et al. "Impaired Metabolic Response to Nerve Stimulation in Brown Adipose Tissue of Hypothyroid Rats." *Mol. Cell. Endocrinol.* 25(1982):213-226.

(56) References Cited

OTHER PUBLICATIONS

Shigekawa et al. "Electroporation of Eukaryotes and Prokaryotes: A General Approach to the Introduction of Macromolecules into Cells." *Biotechniques.* 6.8(1988):742-751.
Shimizu et al. "Sympathetic Activation of Glucose Utilization in Brown Adipose Tissue in Rats." *J. Biochem.* 110.5(1991):688-692.
Solicore Flexicon Batteries Product Line, available at Solicore, Inc. date of first publication unknown, revision 3 date Jan. 2007.
Solicore SF-2529 Product Brochure, date of first publication unknown, revision 2 dated Aug. 2008.
Solicore SF-4823 Product Brochure, date of first publication unknown, revision 2 dated Aug. 2008.
Stylopoulos et al. "Roux-en-Y Gastric Bypass Enhances Energy Expenditure and Extends Lifespan in Diet-Induced Obese Rats." *Obesity.* 17(2009):1839-1847.
*Sustained and Controlled Release Drug Delivery Systems.* Robinson, ed. New York: Marcel Dekker. (1978).
Sutton et al. "Human Immunodeficiency Virus Type 1 Vectors Efficiently Transduce Human Hematopoietic Stem Cells." *J. Virol.* 72.7(1998):5781-5788.
Tajino et al. "Application of Menthol to the Skin of Whole Trunk in Mice Induces Autonomic and Behavorial Heat-Gain Responses." *Am. J. Physiol. Regul. Integr. Comp. Physiol.* 293.5(2007):R2128-2135.
Testerman et al. "Electrical Stimulation as Therapy for Neurological Disorders: The Basics of Implantable Neurological Stimulators." *IEEE Eng. Med. Biol. Mag.* (2006):74-78.
Toii et al. "Fall in Skin Temperature of Exercising Man." *Br. J. Sp. Med.* 26.1(1992):29-32.
U.S. Appl. No. 61/428,013, filed Dec. 29, 2010.
van Marken Lichtenbelt et al. "Cold Activated Brown Adipose Tissue in Healthy Men." *N. Eng. J. Med.* 360(2009):1500-1508.
Virtanen et al. "Functional Brown Adipose Tissue in Healthy Adults." *N. Eng. J. Med.* 360.15(2009):1518-1525.
Wagner et al. "Coupling of Adenovirus to Transferrin-Polylysine/DNA Complexes Greatly Enhances Receptor-Mediated Gene Delivery and Expression of Transfected Genes." *PNAS.* 89.13(1992):6099-6103.
Weidner et al. "Time Course of Post-Excitatory Effects Separates Afferent Human C Fibre Classes." *J. Physiol.* 527(2000):185-191.
Wells et al. "Application of Infrared Light for in vivo Neural Stimulation." *J. Biomed. Opt.* 10.6(2005):064003.
Wells et al. "Biophysical Mechanisms of Transient Optical Stimulation of Peripheral Nerve." *Biophys. J.* 93.7(2007):2567-2580.
Wells et al. "Optical Stimulation of Neural Tissue in vivo." *Opt. Lett.* 30.5(2005):504-506.
Wells et al. "Optically Mediated Nerve Stimulation: Identification of Injury Thresholds." *Lasers Surg. Med.* 39.6(2007):513-526.
Wells et al. "Pulsed Laser Versus Electrical Energy for Peripheral Nerve Stimulation." *J. Neurosci. Meth.* 163.2(2007):326-337.
Wu et al. "A Pilot Study to Evaluate the Effect of Splanchnic Nerve Stimulation on Body Composition and Food Intake in Rats." *Obes. Surg.* 19(2009):1581-1585.
Xiong et al. "Sindbis Virus: An Efficient, Broad Host Range Vector for Gene Expression in Animal Cells." *Science.* 243(1989):1188-1191.
Xu et al. "CMV-β-Actin Promoter Directs Higher Expression from an Adeno-Associated Viral Vector in the Liver than the Cytomegalovirus or Elongation Factor 1α Promoter and Results in Therapeutic Levels of Human Factor X in Mice." *Hum. Gene Ther.* 12.5(2001):563-573.
Ye et al. "Discovery and Activity of (1R, 4S, 64)-N-[(1R)-2-[4-cyclohexyl-4-[[(1,1-dimethylethyl0amino]carbonyl]-1-piperidinyl]-1-[(4-fluorophenyl)methyl]-2-oxoethyl]-2-methyl-2-azabicycylo[2.2.2]octane-6-carboxamide (3,RY764), a Potent and Selective Melanocortin Subtype-4 Receptor Agonist." *Bioorg. Med. Chem. Lett.* 15.15(2005):3501-3505.
Yin et al. "Inhibitory Effects of Intestinal Electrical Stimulation on Food Intake, Weight Loss, and Gastric Emptying in Rats." *Am. J. Physiol. Regul. Integr. Comp. Physiol.* 293.1(2007):R78-R82.
Yoo et al. "The Condrogenic Potential of Human Bone-Marrow-Derived Mesenchymal Progenitor Cells." *J. Bone Joint Surg. Am.* 80.12(1998):1745-1757.
Zhao et al. "A Novel Promoter Controls Cyp19a1 Gene Expression in Mouse Adipose Tissue." *Reprod. Biol. Endocrinol.* 7(2009):37.
Zheng et al. "Stimulation of Sympathetic Innervations in the Upper Gastrointestinal Tract as a Treatment for Obesity." *Med. Hyp.* 72(2009):706-710.
Autonomic and Motor Nervous System' Notes from Principles of Human Physiology Chapter 11. Retrieved 2014 8 pages.
Birks R.I. 'Regulation by patterned preganglionic neural activity of transmitter stores in a sympathetic ganglion' J. Physiol 1978 280 559-572.
Bredenbeek et al 'Sindbis Virus Expression Vectors: Packaging of RNA Replicons by Using Defective Helper RNAs' J. Virol. 67.11 (1993) pp. 6439-6446.
Bugajksi A.J. et al 'Effect of long-term vagal stimulation on food intake and body weight during diet induced obesity in rats' J Phys Pharm (2007) 58 (suppl 1) 5-12.
Cannon, et al 'Brown Adipose Tissue: Function and Physiological Significance' Physiol Rev 2004 84 pp. 277-359.
Cannon, et al 'Nonshivering Thermogenesis and its Adequate Measurement in Metabolic Studies' J. Exp. Biol. 214 (2011) pp. 242-253.
Freeman, P et al 'Brown Adipose Tissue Thermogenesis Induced by Low Level Electrical Stimulation of Hypothalamus in rats' Brain Research Bulletin (1987) Vpo. 18 pp. 7-11.
Molecular Biology of the Cell, 3rd Edition, ed by Alberts et al., New York Garland Publishing (1994) Ch. 19.
Morrison, S.F. RVLM and raphe differentially regulate sympathetic outflows to splanchnic and brown adipose tissue, American Journal of Physiology—Regulatory, Integrative and Comparative Physiology, published Apr. 1, 1999, vol. 276 No. 4 pp. 962-973.
Australian Office Action for Application No. 1010343059, dated Aug. 30, 2013(5pages).
International Preliminary Report on Patentability dated Aug. 2, 2012 for Application No. PCT/US2010/062464 (6 pages).
International Preliminary Report on Patentability dated Jul. 4, 2017 for Application No. PCT/US2015/065513 (7 pages).
International Preliminary Report on Patentability dated Jul. 4, 2017 for Application No. PCT/US2015/065516 (7 pages).
International Search Report and Written Opinion for PCT/US10/62464 dated Feb. 24, 2011 (8 pages).
International Search Report re: PCT/US2015/065513 dated Mar. 9, 2016 (6 pages).
International Search Report re: PCT/US2015/065516 dated Apr. 7, 2016.
Office Action issued in Chinese Application No. 201080065678.8 dated Mar. 21, 2014 (Chinese original and English translation).
Office Action issued in Japanese Application No. 2012-550003 dated Sep. 16, 2014 (Japanese original and English translation).
Supplementary European Search Report re: EP10844295 dated Aug. 1, 2013.
Written Opinion re: PCT/US2015/065516 dated Apr. 7, 2016.

\* cited by examiner

METHODS AND DEVICES FOR INHIBITING NERVES WHEN ACTIVATING BROWN ADIPOSE TISSUE

FIELD OF THE INVENTION

The present invention relates to methods and devices for inhibiting nerves when activating brown adipose tissue.

BACKGROUND OF THE INVENTION

Obesity is becoming a growing concern, particularly in the United States, as the number of people with obesity continues to increase and more is learned about the negative health effects of obesity. Severe obesity, in which a person is 100 pounds or more over ideal body weight, in particular poses significant risks for severe health problems. Accordingly, a great deal of attention is being focused on treating obese patients.

Surgical procedures to treat severe obesity have included various forms of gastric and intestinal bypasses (stomach stapling), biliopancreatic diversion, adjustable gastric banding, vertical banded gastroplasty, gastric plications, and sleeve gastrectomies (removal of all or a portion of the stomach). Such surgical procedures have increasingly been performed laparoscopically. Reduced postoperative recovery time, markedly decreased post-operative pain and wound infection, and improved cosmetic outcome are well established benefits of laparoscopic surgery, derived mainly from the ability of laparoscopic surgeons to perform an operation utilizing smaller incisions of the body cavity wall. However, such surgical procedures risk a variety of complications during surgery, pose undesirable post-operative consequences such as pain and cosmetic scarring, and often require lengthy periods of patient recovery. Patients with obesity thus rarely seek or accept surgical intervention, with only about 1% of patients with obesity being surgically treated for this disorder. Furthermore, even if successfully performed and initial weight loss occurs, surgical intervention to treat obesity may not result in lasting weight loss, thereby indicating a patient's need for additional, different obesity treatment.

Nonsurgical procedures for treating obesity have also been developed. However, effective therapies for increasing energy expenditure and/or altering a patient's metabolism, e.g., a basal metabolic rate, leading to improvements in metabolic outcomes, e.g., weight loss, have focused on pharmaceutical approaches, which have various technical and physiological limitations.

It has been recognized in, for example, U.S. Pat. No. 6,645,229 filed Dec. 20, 2000 and entitled "Slimming Device," that brown adipose tissue (BAT) plays a role in the regulation of energy expenditure and that stimulating BAT can result in patient slimming. BAT activation is regulated by the sympathetic nervous system and other physiological, e.g., hormonal and metabolic, influences. When activated, BAT removes free fatty acids (FFA) and oxygen from the blood supply for the generation of heat. The oxidative phosphorylation cycle that occurs in the mitochondria of activated BAT is shown in FIGS. 1 and 2.

Accordingly, there is a need for improved methods and devices for treating obesity and in particular for activating BAT.

SUMMARY OF THE INVENTION

The present invention generally provides methods and devices for inhibiting nerves when activating brown adipose tissue. In one embodiment, a medical method is provided that includes applying a first neuromodulator to a depot of BAT. The application of the first neuromodulator can cause activation of a first nerve type in the BAT so as to increase energy expenditure of the BAT. The method can also include applying a second neuromodulator to the depot of BAT simultaneously with the application of the first neuromodulator. The application of the second neuromodulator can inhibit a second nerve type in the BAT that is different from the first nerve type.

The method can vary in any number of ways. For example, the first nerve type can include sympathetic nerves, and the second nerve type can include parasympathetic nerves. For another example, the first nerve type can include sympathetic nerves, and the second nerve type can include sensory nerves. For still another example, the application of the second neuromodulator can start before the application of the first neuromodulator begins so as to start inhibiting the second nerve type before the first nerve type is activated. For yet another example, the first neuromodulator can include applying a first electrical signal to the depot of BAT, and applying the second neuromodulator can include applying a second electrical signal to the depot of BAT that is different from the first electrical signal. For another example, applying one of the first and second neuromodulators can include applying an electrical signal to the depot of BAT, and applying the other of the second neuromodulators can include delivering a chemical to the depot of BAT. For still another example, applying the first neuromodulator can include delivering a first chemical to the depot of BAT, and applying the second neuromodulator can include delivering a second chemical to the depot of BAT that is different from the first chemical. For another example, applying the first neuromodulator can include at least one of applying an electrical signal to the depot of BAT, delivering a chemical to the depot of BAT, cooling the depot of BAT, and applying a light to the depot of BAT, and applying the second neuromodulator can include at least one of applying a different electrical signal to the depot of BAT and delivering a different chemical to the depot of BAT.

In another embodiment, a medical method can include neuromodulating a sympathetic nervous system of a patient proximate to a depot of BAT of a patient so as to activate the BAT and increase energy expenditure of the BAT, and simultaneously with the neuromodulating of the sympathetic nervous system, suppressing a parasympathetic nervous system of the patient proximate to the depot of brown adipose tissue.

The method can have any number of variations. For example, neuromodulating the sympathetic nervous system can activate sympathetic nerves innervating the BAT, and suppressing the parasympathetic nervous system can suppress parasympathetic nerves innervating the BAT. Each of the parasympathetic nerves can have a larger diameter than each of the sympathetic nerves. For another example, the suppression of the parasympathetic nervous system begins before the neuromodulation of the sympathetic nervous system so as to start suppressing the parasympathetic nervous system before the sympathetic nervous system is neuromodulated. For still another example, neuromodulating the sympathetic nervous system can include delivering a first chemical to the patient. Suppressing the parasympathetic nervous system can include one of delivering a second chemical to the patient that is different than the first chemical and applying an electrical signal to the patient. For yet another example, neuromodulating the sympathetic nervous system can include at least one of applying an electrical signal to the patient, delivering a chemical to the patient, cooling the patient, and applying a light to the patient.

For another example, neuromodulating the sympathetic nervous system can include applying a first electrical signal to the patient. In some embodiments, suppressing the parasympathetic nervous system can include applying a second electrical signal to the patient that is different than the first electrical signal. The second electrical signal can have a variety of configurations. For example, a current of the first electrical signal can be in a range of ten to one hundred times greater than a current of the second electrical signal. For another example, the second electrical signal can include one of a hyperpolarizing lower energy pulse as compared to the first electrical signal, and a depolarizing lower energy pulse as compared to the first electrical signal. In some embodiments, suppressing the parasympathetic nervous system can include applying a chemical to the patient.

In another aspect, a medical apparatus is provided that in one embodiment includes at least one electrode configured to directly contact a tissue of a patient proximate to a depot of BAT and to simultaneously deliver first and second electrical signals to the patient. The first electrical signal can be configured to cause activation of a first nerve type in the BAT so as to increase energy expenditure of the BAT. The second electrical signal can be configured to inhibit a second nerve type in the BAT that is different from the first nerve type. The apparatus can also include at least one signal generator in electronic communication with the at least one electrode and configured to generate the first and second electrical signals delivered by the at least one electrode. The apparatus can have any number of variations.

BRIEF DESCRIPTION OF THE DRAWINGS

The invention will be more fully understood from the following detailed description taken in conjunction with the accompanying drawings, in which.

DETAILED DESCRIPTION OF THE INVENTION

Figure 1:
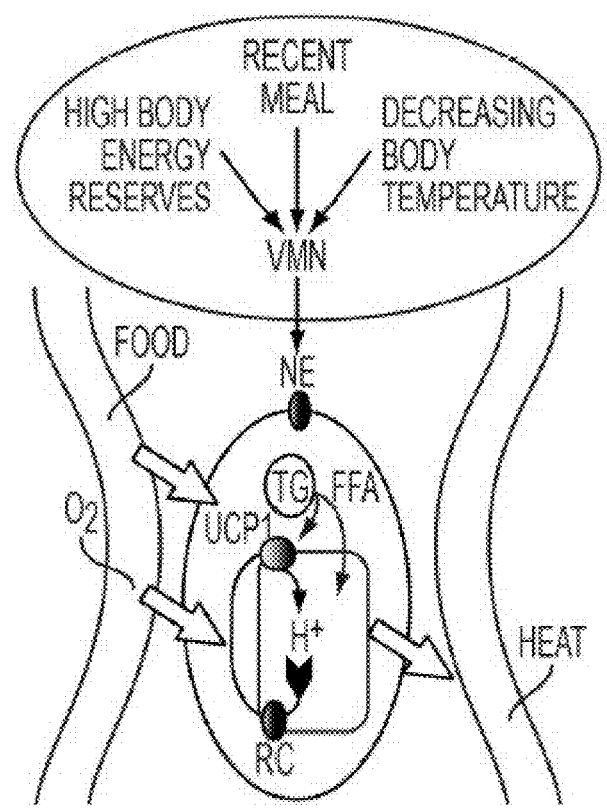
FIG. 1 is a schematic view of an oxidative phosphorylation cycle that occurs in mitochondria within BAT cells.
Figure 2:
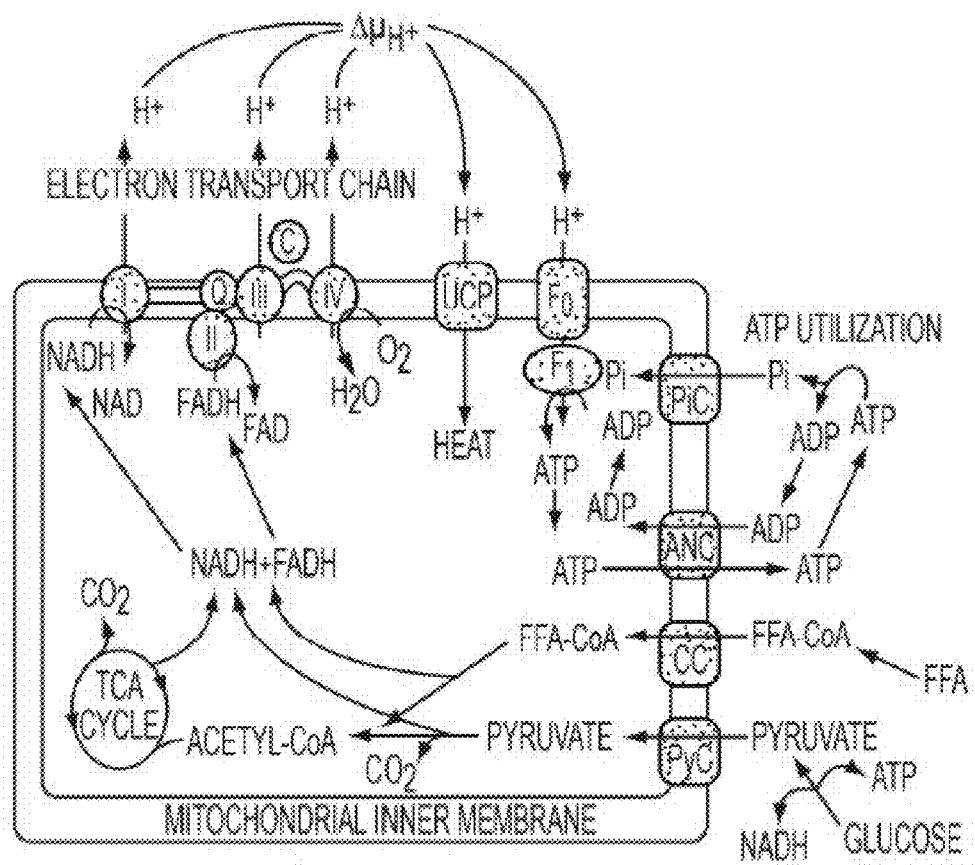
FIG. 2 is a schematic view of BAT mitochondria showing an oxidative phosphorylation cycle that occurs in the mitochondria.

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Various exemplary methods and devices are provided for inhibiting nerves when activating brown adipose tissue (BAT). In general, the methods and devices can facilitate activation of BAT to increase thermogenesis, e.g., increase heat production and energy expenditure in the patient, which over time can lead to one or more of weight loss, a change in the metabolism of the patient, e.g., increasing the patient's basal metabolic rate, and improvement of comorbidities associated with obesity, e.g., Type II diabetes, high blood pressure, etc. In this way, weight loss, increased metabolic rate, and/or comorbidity improvement can be induced without performing a major surgical procedure, without relying on administration of one or more pharmaceuticals, without relying on cooling of the patient, and without surgically altering a patient's stomach and/or other digestive organs. A first nerve type (e.g., sympathetic nerves) innervating BAT can be activated while at least one other nerve type (e.g., parasympathetic nerves and/or sensory nerves) innervating BAT is being suppressed. In general, a first neuromodulator (e.g., an electrical signal, a chemical, a light, cooling, mechanical manipulation or vibration, a magnetic field, etc.) can be applied to activate the first nerve type, and a second neuromodulator can be applied to inhibit the at least one other nerve type. In this way, parasympathetic nerves and/or sensory nerves innervating BAT can be inhibited when activating sympathetic nerves innervating BAT. The second neuromodulator can be applied before the first neuromodulator so as to start inhibiting the at least one other nerve type before the first nerve type begins to be activated by the first neuromodulator. Starting the inhibition of the at least one other nerve type before the first nerve type begins to be activated can help prevent the first neurotransmitter from activating the at least one other nerve type, e.g., due to an electrical or light signal being applied by the first neurotransmitter having sufficient strength to activate the first nerve type and the at least one other nerve type (absent the at least one other nerve type's prior inhibition). The first and second neuromodulators can be applied simultaneously, which can facilitate inhibition of the at least one other nerve type throughout the activation of the first nerve type.

Sympathetic nerves innervating BAT can be activated using at least one neuromodulator (e.g., electrical energy, a light, cooling, a chemical, mechanical manipulation or vibration, a magnetic field, etc.) to increase energy expenditure, as discussed further below. In rodents, parasympathetic nerves can be found in paravertebral BAT depots, but not in intrascapular BAT depots. In humans, parasympathetic nerves may be found in paravertebral BAT depots and in supraclavicular BAT depots. Parasympathetic nerves (also referred to as craniosacral nerves and cholinergic nerves) of a human's parasympathetic nervous system can also innervate the BAT, and the parasympathetic nerves can be activated by the neuromodulator that is activating the sympathetic nerves. As will be appreciated by a person skilled in the art, the sympathetic nervous system and the parasympathetic nervous system generally function opposite to one another in complementary fashion. The sympathetic nervous system typically functions in actions requiring quick responses, while the parasympathetic nervous typically functions in actions that do not require immediate reactions. If both of the sympathetic and parasympathetic nervous systems are activated, the parasympathetic nervous system will generally oppose the actions of the sympathetic nervous system. Accordingly, if both sympathetic and parasympathetic nerves are activated when attempting to activate BAT, the parasympathetic nerve activation can attenuate the effects of the sympathetic nerve stimulation. Thus, the advantageous effect(s) that can result from activating the BAT, e.g., from activating the sympathetic nerves, can be reduced and, in some instances, can be eliminated entirely due to the parasympathetic nerve activation. Accordingly, activating BAT to activate the sympathetic nerves and inhibiting the parasympathetic nerves can allow the BAT activation to provide the advantageous effect(s) of BAT activation without being partially or fully suppressed due to parasympathetic nerve activation.

Sensory nerves (e.g., pressure sensitive nerves and temperature sensitive nerves) can innervate BAT. The sensory nerves can be activated when attempting to activate the BAT, e.g., a temperature change caused by the neuromodulator can trigger temperature sensitive nerves. The activation of the sensory nerves can serve in a feedback loop that can attenuate the effects of the stimulation of the sympathetic nerves as a natural defense mechanism attempting to prevent the body from being harmed by the unexpected activation, the source of which the body generally does not know. Thus, similar to that discussed above regarding parasympathetic nerves, activating the sensory nerves when attempting to activate the BAT can adversely affect the BAT activation. Accordingly, neuromodulating the sympathetic nerves to activate the BAT while inhibiting the sensory nerves can allow the BAT activation to provide the advantageous effect(s) of BAT activation without being partially or fully suppressed due to sensory nerve activation.

Parasympathetic and sympathetic nerves form an efferent pathway including preganglionic and postganglionic neurons. Second-order postganglionic neurons synapse on smooth and cardiac muscle and also control glandular secretion. In addition to preganglionic and postganglionic neurons, control systems of the autonomic nervous system (ANS), which includes the sympathetic and parasympathetic nervous systems, also involve supraspinal controlling and integrative neuronal centers; supraspinal, spinal, ganglionic, and peripheral interneurons; and afferent neurons. Afferent neurons have cell bodies in the dorsal root ganglia or cranial nerve somatic sensory ganglia. Afferent axons travel in somatic peripheral nerves or along with autonomic efferent nerves.

The parasympathetic preganglionic component of the ANS has a supraspinal and spinal portion. Parasympathetic preganglionic neurons are found in four parasympathetic brain stem nuclei: nucleus Edinger-Westphal, superior salivatory nucleus, inferior salivatory nucleus, and the dorsal vagal complex of the medulla. Their axons exit via cranial nerves 3 (oculomotor); 7 (facial nerve); 9 (glossopharyngeal nerve); and 10 (vagus nerve) respectively. Parasympathetic preganglionic neurons are also found in the intermediolateral (IML) cell column of the sacral spinal cord in segments S2-S4 and exit the central nervous system (CNS) via the sacral ventral roots and the spinal nerves and then continue to the pelvic viscera as the pelvic nerve. The sacral preganglionic parasympathetic efferent axons of the pelvic nerve synapse with postganglionic parasympathetic neurons in the ganglia of the pelvic plexus. Postganglionic axons innervate the descending colon, rectum, urinary bladder, and sexual organs.

The sympathetic preganglionic component of the ANS is purely spinal. Sympathetic preganglionic neurons (SPNs) are found in the IML cell column of the thoracic and lumbar spinal cord in segments T1-L2 and exit the CNS via the thoracolumbar ventral roots. The sympathetic segmental outflow can vary, and the outflow can start as high as C8 or as low as T2 and end at L1 or L3. The thinly myelinated preganglionic fibers exit via the ventral roots as the white rami communicantes. Many sympathetic preganglionic fibers synapse in the paravertebral ganglia, which are paired and lie next to the spine from the cervical to the sacral segments. There are three cervical paravertebral ganglia: the superior cervical ganglion, the middle cervical ganglion, and the stellate ganglion. There are usually eleven thoracic ganglia, four lumbar ganglia, and four or five sacral ganglia. Sympathetic preganglionic axons can synapse in paravertebral ganglia at the segment of their exit or can pass up or down several segments of the sympathetic chain before synapsing. One sympathetic preganglionic axon will synapse with several postganglionic neurons. Postganglionic axons are unmyelinated, small diameter fibers that leave the paravertebral ganglia via the gray rami communicantes and exit via the segmental spinal nerves.

Some sympathetic preganglionic axons pass through the paravertebral ganglia without synapsing and constitute the splanchnic nerves that innervate three prevertebral ganglia: celiac ganglion, superior mesenteric ganglion, and inferior mesenteric ganglion (IMG), as well as the adrenal medulla. Postsynaptic axons from the prevertebral ganglia course to the abdominal and pelvic viscera as the hypogastric, splanchnic, and mesenteric plexuses.

Sweat glands, piloerector muscles, and most small blood vessels receive only sympathetic innervation. Diffuse sympathetic nervous system discharge results in pupillary dilatation, increased heart rate and contractility, bronchodilation, vasoconstriction of the mesenteric circulation, and vasodilation of skeletal muscle arterioles. This is the "fight or flight" defense reaction.

Supraspinal neurons involved in the control systems of the ANS are located in the nucleus of the tractus solitarius (NTS), nucleus ambiguus, dorsal motor nucleus of vagus, dorsal raphe nucleus, medullary reticular formation nuclei, locus ceruleus, hypothalamus, limbic system, and the primary sensory and motor cortex. The hypothalamus has uncrossed sympathetic descending pathways to the midbrain, lateral pons, and medullary reticular formation. Descending reticulospinal pathways from the pons and medulla to interneurons in the spinal cord influence the IML cells. The NTS receives afferents from the viscera and functions as an integrating center for reflex activity as well as a relay station to the hypothalamus and limbic systems.

At the effector organs, sympathetic ganglionic neurons release noradrenaline (norepinephrine), along with other cotransmitters such as adenosine triphosphate (ATP), to act on adrenergic receptors, with the exception of the sweat glands and the adrenal medulla. Acetylcholine is the preganglionic neurotransmitter for both divisions of the ANS, as well as the postganglionic neurotransmitter of parasympathetic neurons. Nerves that release acetylcholine are said to be cholinergic. In the parasympathetic system, ganglionic neurons use acetylcholine as a neurotransmitter, to stimulate muscarinic receptors. At the adrenal cortex, there is no postsynaptic neuron. Instead, the presynaptic neuron releases acetylcholine to act on nicotinic receptors. Stimulation of the adrenal medulla releases adrenaline (epinephrine) into the bloodstream which will act on adrenoceptors, producing a widespread increase in sympathetic activity. Blocking either the release of acetylcholine from these nerves, or blocking the binding of this neurotransmitter to the receptors on BAT with an anticholinergic agent can help suppress parasympathetic activity, thereby improving the effectiveness of the BAT neuromodulation. This blocking can be done locally or globally.

Following a surgical procedure to treat obesity such as Roux-en-Y gastric bypass (RYGB), a patient can lose weight due to an increase in energy expenditure, as demonstrated in a rodent model for example in Stylopoulos et al., "Rouxen-Y Gastric Bypass Enhances Energy Expenditure And Extends Lifespan In Diet-Induced Obese Rats," *Obesity* 17 (1 Oct. 2009), 1839-47. Additional data from Stylopoulos et al. (not published in the previous article or elsewhere as of the filing date of the present application) indicates that RYGB is also associated with increased levels of uncoupling protein 1 (UCP1), which is an uncoupling protein in mitochondria of BAT, as well as with a significant reduction in the size of fat stores within BAT and an increased volume of BAT. It thus appears that RYGB causes activation of BAT, although as discussed above, surgical procedures to treat obesity, such as gastric bypass, risk if not necessarily cause a variety of undesirable results in at least some patients. Devices and methods to activate BAT, without a major surgical procedure like RYGB, to increase energy expenditure are therefore provided.

One characteristic of BAT that distinguishes it from white adipose tissue (WAT) stores is the high number of mitochondria in a single BAT cell. This characteristic makes BAT an excellent resource for burning energy. Another distinguishing characteristic of BAT is that when activated, UCP1 is utilized to introduce inefficiency into the process of adenosine triphosphate (ATP) creation that results in heat generation. Upregulation of UCP1 is therefore a marker of BAT activation.

Activation of brown adipocytes leads to mobilization of fat stores within these cells themselves. It also increases transport of FFA into these cells from the extracellular space and bloodstream, particularly when the local reserves that are associated with BAT are depleted. FFAs in the blood are derived primarily from fats metabolized and released from adipocytes in WAT as well as from ingested fats. Stimulation of the sympathetic nervous system is a major means of physiologically activating BAT. Sympathetic nerve stimulation also induces lipolysis in WAT and release of FFA from WAT into the bloodstream to maintain FFA levels. In this way, sympathetic stimulation leads ultimately to the transfer of lipids from WAT to BAT followed by oxidation of these lipids as part of the heat generating capacity of BAT. This activation of brown adipocytes can also lead to improvements in diabetes related markers.

The controlled activation of BAT can be optimized, leading to weight loss, increased metabolic rate, and/or comorbidity improvement, by reducing the stores of triglycerides in WAT. BAT can be activated in a variety of ways. For non-limiting example, a pharmaceutical can be administered to a patient, the patient can be cooled, the patient can be heated, a magnetic field can be targeted to a region of a patient, a BAT-neuromodulation procedure can be performed on the patient directed to a BAT depot and/or to a nerve innervating BAT, the patient can engage in weight loss therapies, and/or a surgical procedure can be performed on the patient, such as a procedure to induce weight loss and/or to improve metabolic function, e.g., glucose homeostatis, lipid metabolism, immune function, inflammation/anti-inflammatory balance, etc. Non-limiting examples of a neuromodulation technique configured to activate a nerve innervating BAT include delivery of a medium to the nerve that induces an action potential in the nerve, e.g., electricity, light, mechanical manipulation or vibration, a magnetic field, a chemical, etc. Non-limiting examples of a BAT-neuromodulation procedure include inducing differentiation of muscle, WAT, preadipocytes, or other cells to BAT, and/or implanting or transplanting BAT cells into a patient. Non-limiting examples of implanting or transplanting BAT cells include removing cells from a patient, culturing the removed cells, and reimplanting the cultured cells; transplanting cells from another patient; implanting cells grown from embryonic stem cells, adult stem cells, or other sources; and genetically, pharmacologically, or physically altering cells to improve cell function. Non-limiting examples of such weight loss therapies include a prescribed diet and prescribed exercise. Non-limiting examples of such a surgical procedure include gastric bypass, biliopancreatic diversion, a gastrectomy (e.g., vertical sleeve gastrectomy, etc.), adjustable gastric banding, vertical banded gastroplasty, intragastric balloon therapy, gastric plication, Magenstrasse and Mill, small bowel transposition, biliary diversion, vagal nerve stimulation, gastrointestinal barrier (e.g., duodenal endoluminal barrier, etc.), and procedures that allow for removal of food from the gastrointestinal tract. Combining one or more treatments, particularly a weight loss therapy or a weight loss surgical procedure which does not activate BAT, e.g., a procedure other than RYGB, biliopancreatic diversion (BPD) with or without duodenal switch, or some duodenal or other intestinal barrier (e.g., a prescribed diet and/or exercise program, adjustable gastric banding, vertical banded gastroplasty, sleeve gastrectomy, gastric plication, Magenstrasse and Mill, intragastric balloon therapy, some duodenal or other intestinal barrier, and small bowel transposition, with a means for acute or chronic activation of BAT such as the neuromodulation discussed herein, can result in desirable patient outcomes through a combined approach.

In some embodiments, exposure to cold temperature can lead to the activation of BAT to help regulate body temperature. Exemplary embodiments of using cooling to activate BAT are described in U.S. application Ser. No. 13/977,555 entitled "Methods And Devices For Activating Brown Adipose Tissue With Cooling" filed Jun. 28, 2013, which is hereby incorporated by reference in its entirety. In some embodiments, BAT can be activated by being electrically stimulated. Exemplary embodiments of using electrical stimulation to activate BAT are described in more detail in U.S. Pat. Pub. No. 2011/0270360 entitled "Methods And Devices For Activating Brown Adipose Tissue Using Electrical Energy" filed Dec. 29, 2010, which is hereby incorporated by reference in its entirety. In some embodiments, BAT can be activated using light. Exemplary embodiments of using light to activate BAT are described in more detail in U.S. Pat. Pub. No. 2014/0088487 entitled "Methods And Devices For Activating Brown Adipose Tissue Using Light" filed Jun. 28, 2013, which is hereby incorporated by reference in its entirety. In some embodiments, BAT can be chemically activated. Exemplary embodiments of using one or more chemicals to activate BAT are described in more detail in U.S. Pat. Pub. No. 2014/0018767 entitled "Methods And Devices For Activating Brown Adipose Tissue With Targeted Substance Delivery" filed Jun. 28, 2013, which is hereby incorporated by reference in its entirety. In some embodiments, brown adipocytes can be modified to increase activation of BAT, e.g., increasing a number of BAT adipocytes or increasing activation of BAT by modifying brown adipocytes to express a gene that activates brown adipocytes, such as UCP1. Exemplary embodiments of using modifying brown adipocytes to increase activation of BAT are described in more detail in U.S. Pat Pub. No. 2014/0199278 entitled "Brown Adipocyte Modification" filed Jun. 28, 2013, which is hereby incorporated by reference in its entirety. One or more techniques to activate BAT can be used at a time, e.g., a patient can be cooled and electrically stimulated.

A person skilled in the art will appreciate that adult humans have substantial BAT depots, as indicated, for example, in J. M. Heaton, "The Distribution Of Brown Adipose Tissue In The Human," *J Anat.*, 1972 May, 112(Pt 1): 35-39, and W. D. van Marken Lichtenbelt et al, "Cold-Activated Brown Adipose Tissue in Healthy Men," N. Engl. J. Med., 2009 April, 360, 1500-1508. A person skilled in the art will also appreciate that BAT is heavily innervated by the sympathetic nervous system, as indicated, for example, in Lever et al., "Demonstration Of A Catecholaminergic Innervation In Human Perirenal Brown Adipose Tissue At Various Ages In The Adult," *Anat Rec.*, 1986 July, 215(3): 251-5, 227-9. Further, "[t]he thin unmyelinated fibers that contain norepinephrine (and not NPY) are those that actually innervate the brown adipocytes themselves. They form a dense network within the tissue, being in contact with each brown adipocyte (bouton-en-passant), and their release of norepinephrine acutely stimulates heat production and chronically leads to brown adipose tissue recruitment." B. Cannon, and J. Nedergaard, "Brown Adipose Tissue: Function And Physiological Significance," *Physiol Rev.*, 2004: 84: 277-359.

Nerves innervating BAT can be neuromodulated to activate UCP1 and hence increase energy expenditure through heat dissipation through transcutaneous and/or direct neuromodulation of nerves innervating BAT. Transcutaneous and direct neuromodulation are each discussed below in more detail.

Because BAT activation may lead to an increase in body temperature locally, regionally, or systemically, transcutaneous and/or direct neuromodulation of nerves innervating BAT can be combined with one or more heat dissipation treatments, before and/or after transcutaneous and/or direct neuromodulation of BAT. Non-limiting examples of such a heat dissipation treatment include inducing cutaneous/peripheral vasodilation, e.g., local or systemic administration of Alpha antagonists or blockers, direct thermal cooling, etc.

Figure 3:
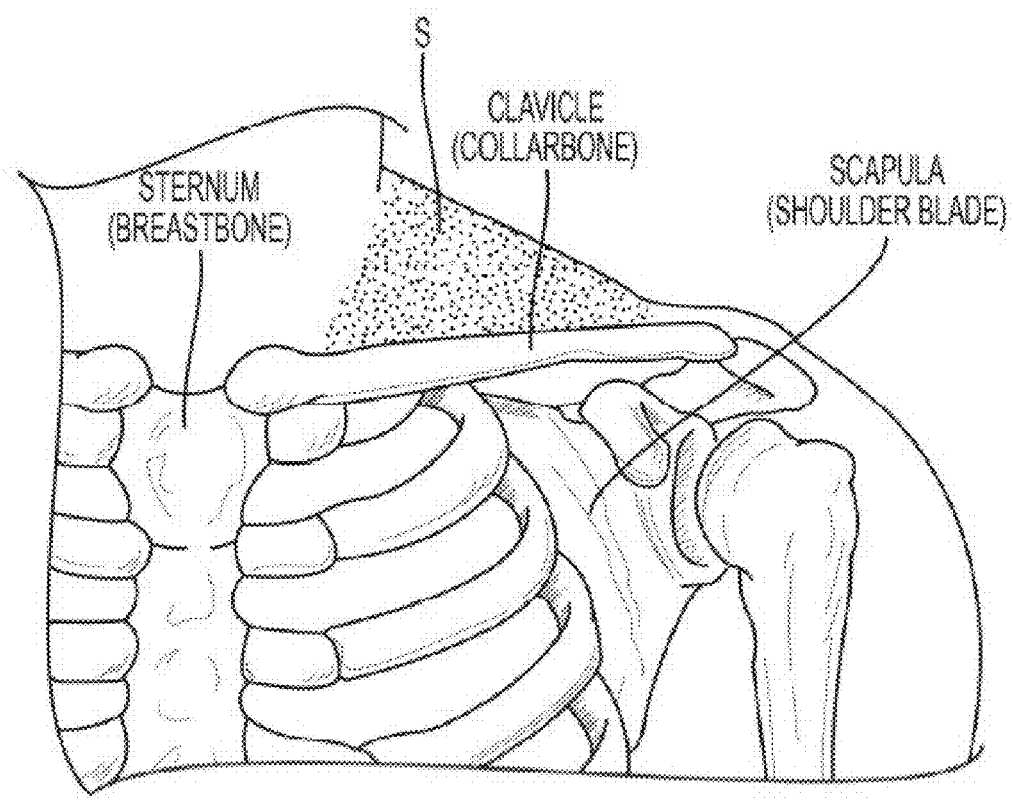
FIG. 3 is a transparent view of a portion of a human neck, chest, and shoulder area with a shaded supraclavicular region.

Whether BAT is activated directly and/or transcutaneously, target areas for BAT nerve neuromodulation and/or direct neuromodulation of brown adipocytes can include areas proximate to BAT depots, e.g., a supraclavicular region, the nape of the neck, over the scapula, alongside the spinal cord, near proximal branches of the sympathetic nervous system that terminate in BAT depots, and around at least one of the kidneys. Any BAT depot can be selected for activation. For non-limiting example, in one embodiment illustrated in FIG. 3, a device (not shown) configured to neuromodulate BAT, e.g., using electricity, can be positioned proximate to an area over a scapula in a supraclavicular region S.

Various exemplary embodiments of transcutaneous devices configured to apply an electrical signal or other neuromodulation means to activate nerves are described in more detail in U.S. Pat. Pub. No. 2011/0270360 entitled "Methods And Devices For Activating Brown Adipose Tissue Using Electrical Energy" filed Dec. 29, 2010, U.S. Pat. Pub. No. 2009/0132018 filed Nov. 16, 2007 and entitled "Nerve Stimulation Patches And Methods For Stimulating Selected Nerves," U.S. Pat. Pub. No. 2008/0147146 filed Dec. 19, 2006 and entitled "Electrode Patch And Method For Neurostimulation," U.S. Pat. Pub. No. 2005/0277998 filed Jun. 7, 2005 and entitled "System And Method For Nerve Stimulation," U.S. Pat. Pub. No. 2006/0195153 filed Jan. 31, 2006 and entitled "System And Method For Selectively Stimulating Different Body Parts," U.S. Pat. Pub. No. 2007/0185541 filed Aug. 2, 2006 and entitled "Conductive Mesh For Neurostimulation," U.S. Pat. Pub. No. 2006/0195146 filed Jan. 31, 2006 and entitled "System And Method For Selectively Stimulating Different Body Parts," U.S. Pat. Pub. No. 2008/0132962 filed Dec. 1, 2006 and entitled "System And Method For Affecting Gastric Functions," U.S. Pat. Pub. No. 2008/0147146 filed Dec. 19, 2006 and entitled "Electrode Patch And Method For Neurostimulation," U.S. Pat. Pub. No. 2009/0157149 filed Dec. 14, 2007 and entitled "Dermatome Stimulation Devices And Methods," U.S. Pat. Pub. No. 2009/0149918 filed Dec. 6, 2007 and entitled "Implantable Antenna," U.S. Pat. Pub. No. 2009/0132018 filed Nov. 16, 2007 and entitled "Nerve Stimulation Patches And Methods For Stimulating Selected Nerves," U.S. Pat. Pub. No. 2010/0161001 filed Dec. 19, 2008 and entitled "Optimizing The Stimulus Current In A Surface Based Stimulation Device," U.S. Pat. Pub. No. 2010/0161005 filed Dec. 19, 2008 and entitled "Optimizing Stimulation Therapy Of An External Stimulating Device Based On Firing Of Action Potential In Target Nerve," U.S. Pat. Pub. No. 2010/0239648 filed Mar. 20, 2009 and entitled "Self-Locating, Multiple Application, And Multiple Location Medical Patch Systems And Methods Therefor," U.S. Pat. Pub. No. 2011/0094773 filed Oct. 26, 2009 and entitled "Offset Electrode," and U.S. Pat. No. 8,812,100 filed May 10, 2012 and entitled "A Device And Method For Self-Positioning Of A Stimulation Device To Activate Brown Adipose Tissue Depot In Supraclavicular Fossa Region."

Various exemplary embodiments of devices configured to directly apply a signal to neuromodulate nerves are described in more detail in U.S. Pat. Pub. No. 2011/02700360 entitled "Methods And Devices For Activating Brown Adipose Tissue Using Electrical Energy" filed Dec. 29, 2010, U.S. Pat. Pub. No. 2005/0177067 filed Jan. 26, 2005 and entitled "System And Method For Urodynamic Evaluation Utilizing Micro-Electronic Mechanical System," U.S. Pat. Pub. No. 2008/0139875 filed Dec. 7, 2006 and entitled "System And Method For Urodynamic Evaluation Utilizing Micro Electro-Mechanical System Technology," U.S. Pat. Pub. No. 2009/0093858 filed Oct. 3, 2007 and entitled "Implantable Pulse Generators And Methods For Selective Nerve Stimulation," U.S. Pat. Pub. No. 2010/0249677 filed Mar. 26, 2010 and entitled "Piezoelectric Stimulation Device," U.S. Pat. Pub. No. 2005/0288740 filed Jun. 24, 2004 and entitled, "Low Frequency Transcutaneous Telemetry To Implanted Medical Device," U.S. Pat. No. 7,599,743 filed Jun. 24, 2004 and entitled "Low Frequency Transcutaneous Energy Transfer To Implanted Medical Device," U.S. Pat. No. 7,599,744 filed Jun. 24, 2004 and entitled "Transcutaneous Energy Transfer Primary Coil With A High Aspect Ferrite Core," U.S. Pat. No. 7,191,007 filed Jun. 24, 2004 and entitled "Spatially Decoupled Twin Secondary Coils For Optimizing Transcutaneous Energy Transfer (TET) Power Transfer Characteristics," and European Pat. Pub. No. 377695 published as International Pat. Pub. No. WO1989011701 published Nov. 30, 2004 and entitled "Interrogation And Remote Control Device."

Identification of one or more BAT depots for activation can be determined on an individualized patient basis by locating BAT depots in a patient by imaging or scanning the patient using PET-CT imaging, tomography, thermography, MRI, or any other technique, as will be appreciated by a person skilled in the art. Non-radioactive based imaging techniques can be used to measure changes in blood flow associated with the activation of BAT within a depot. In one embodiment, a contrast media containing microbes can be used to locate BAT. The contrast media can be injected into a patient whose BAT has been activated. An energy sources such as low frequency ultrasound can be applied to the region of interest to cause destruction of bubbles from the contrast media. The rate of refill of this space can be quantified. Increased rates of refill can be associated with active BAT depots. In another embodiment, a contrast media containing a fluorescent media can be used to locate BAT. The contrast media can be injected into a patient whose BAT has been activated. A needle based probe can be placed in the region of interest that is capable of counting the amount of fluorescent contrast that passes the probe. Increased counts per unit time correspond to increased blood flow and can be associated with activated BAT depots. Because humans can have a relatively small amount of BAT and because it can be difficult to predict where BAT is most prevalent even near a typical BAT depot such as the nape of the neck, imaging a patient to more accurately pinpoint BAT depots can allow more nerves innervating BAT to be activated and with greater precision. Any number of BAT depots identified through patient imaging can be marked for future reference using a permanent or temporary marker. As will be appreciated by a person skilled in the art, any type of marker can be used to mark a BAT depot, e.g., ink applied on and/or below the epidermis, a dye injection, etc. The marker can be configured to only be visible under special lighting conditions such as an ultraviolet light, e.g., a black light.

Whether BAT is activated directly and/or transcutaneously, target cellular areas for BAT nerve activation and/or direct activation of brown adipocytes can include cell surface receptors (e.g., TGR5, $\beta_1$AR, $\beta_2$AR, $\beta_3$AR, etc.), nuclear receptors (e.g., PPAR$\gamma$, FXR, RXR, etc.), transcription co-activators and co-repressors (e.g., PGC1$\alpha$, etc.), intracellular molecules (e.g., 2-deiodinase, MAP kinase, etc.), UCP1 activators, individual cells and related components (e.g., cell surface, mitochondria, and organelles), transport proteins, PKA activity, perilipin and HSL (phospho PKA substrate), CREBP (cAMP response element-binding protein), adenosine monophosphate-activated protein kinase (AMPK), bile acid receptors (e.g., TGR5, FGF15, FXR, RXR $\alpha$, etc.), muscarinic receptors, etc.

In the course of treating a patient, BAT nerves and/or brown adipocytes can be neuromodulated at any one or more BAT depots directly or indirectly and can be neuromodulated simultaneously, e.g., two or more BAT depots being concurrently activated, or activated sequentially, e.g., different BAT depots being activated at different times. Simultaneous neuromodulation of BAT can help encourage more and/or faster energy expenditure. Sequential neuromodulation of BAT can help prevent the "burning out" of target nerves and can help stimulate the creation of new BAT cells. Sequential nerve neuromodulation can include activating the same BAT depot more than once, with at least one other BAT depot being activated before activating a previously activated BAT depot. Simultaneous and/or sequential neuromodulation can help prevent tachypylaxis.

BAT and the nerves innervating BAT can each be neuromodulated transcutaneously (e.g., from outside a patient's body) or directly (e.g., by direct contact therewith). For a subcutaneous example, a neuromodulator can be fully implanted within a patient to be in direct contact with a BAT depot to allow activation of the BAT depot. For another subcutaneous example, a neuromodulator can be fully implanted within a patient to be in direct contact with a nerve innervating a BAT depot to allow activation of the nerve. For a percutaneous example, a neuromodulator can be partially implanted within a patient to be in direct contact with a BAT depot to allow activation of the BAT depot, e.g., an external skin patch including at least one electrode positioned on a skin surface of a patient with at least one conductor extending from the at least one electrode and through the skin surface to the BAT depot, an external skin patch including at least one electrode positioned on a skin surface of a patient with at least one light-emitting fiber optic wire extending from the at least one electrode and through the skin surface to the BAT depot, etc. For another percutaneous example, a neuromodulator can be partially implanted within a patient to be in direct contact with a nerve innervating a BAT depot to allow activation of the nerve, e.g., an external skin patch including at least one electrode positioned on a skin surface of a patient with at least one conductive needle extending from the at least one electrode and through the skin surface to the nerve, an external skin patch including at least one electrode positioned on a skin surface of a patient with at least one light-emitting fiber optic wire extending from the at least one electrode and through the skin surface to the nerve, etc. For a transcutaneous example, a neuromodulator can be positioned external to a patient proximate a BAT depot to allow activation thereof, e.g., an external skin patch including at least one electrode positioned on a skin surface of a patient with a conductive gel coupled to the at least one electrode, etc.

Regardless of whether the BAT or nerves innervating BAT are neuromodulated transcutaneously or directly using one or more neuromodulation means (e.g., electricity, light, mechanical manipulation or vibration, a magnetic field, a chemical substance, etc.) so as to activate sympathetic nerves innervating the BAT, at least one other nerve type innervating the BAT can be inhibited, as mentioned above.

In one exemplary embodiment, the BAT can be activated using a first electrical signal and a second electrical signal. The first electrical signal can be configured to stimulate the sympathetic nerves, and the second electrical signal can be configured to inhibit the other nerve type, e.g., to inhibit parasympathetic nerves and/or sensory nerves. Both of the first and second electrical signals can be delivered transcutaneously, which can facilitate application of the first and second electrical signals by allowing the first and second electrical signals to be delivered using the same device applied transcutaneously to a patient. In another embodiment, both of the first and second electrical signals can be directly delivered, which can allow for unobtrusive BAT stimulation. In an exemplary embodiment, the second electrical signal can begin to be applied to the BAT before the first electrical signal is applied to the BAT which can prevent the first electrical signal from activating the other nerve type when applied to the BAT, e.g., due to the first electrical signal having sufficient strength to activate the sympathetic nerves and the other nerve type (absent the at least one other nerve type's prior inhibition).

Figure 4:
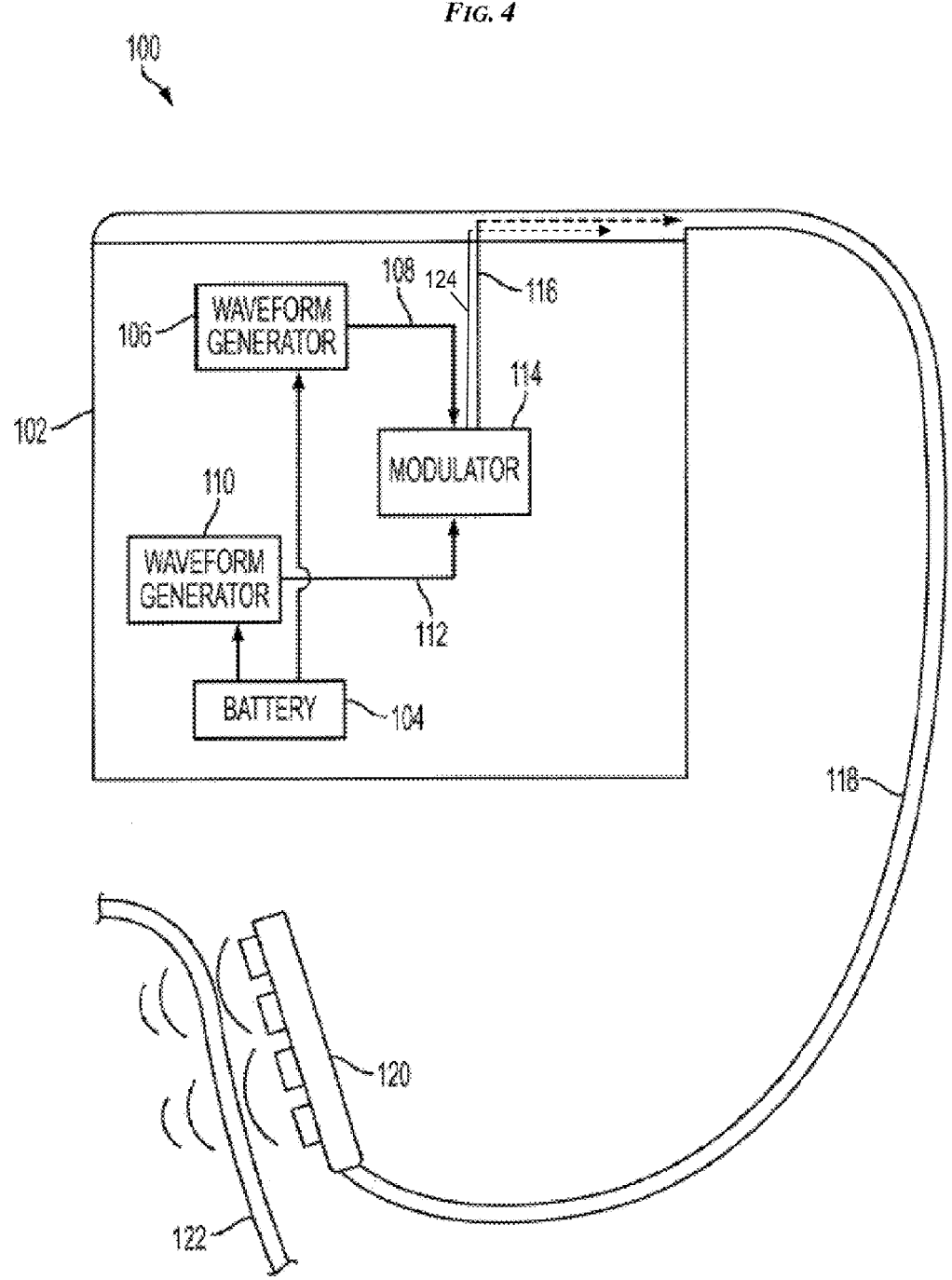
FIG. 4 is a schematic view of one embodiment of an implantable device for activating BAT.

FIG. 4 illustrates one exemplary embodiment of an implantable device 100 configured to generate and deliver an electrical signal to tissue such as BAT. The implantable device 100 can be fully implanted within a patient's body, or the device 100 can be only partially implanted within a patient's body (e.g., be percutaneous) so as to be at least partially located outside the patient's body. The implantable device 100 can include a housing 102 coupled to a suitable power source or battery 104 such as a lithium battery, a first waveform generator 106, and a second waveform generator 110. As in the illustrated embodiment, the battery 104 and the first and second waveform generators 106, 110 can be located within the housing 102. In another embodiment, a battery can be external to a housing and be wired or wirelessly coupled thereto. The housing 102 is preferably made of a biocompatible material. The first and second waveform generators 106, 110 can be electrically coupled to and powered by the battery 104. The waveform generators 106, 110 can be of any suitable type, such as those sold by Texas Instruments of Dallas, Tex. under model number NE555. The first waveform generator 106 can be configured to generate a first waveform or low frequency modulating signal 108, and the second waveform generator 110 can be configured to generate a second waveform or carrier signal 112 having a higher frequency than the first waveform 108. The carrier signal 112 can make it easier to stimulate BAT and/or nerves innervating BAT by using less energy, and/or can make the electrical signal more comfortable for the patient. The first waveform 108 cannot easily, in and of themselves, pass through body tissue to effectively stimulate target nerves. The second waveform 112 can, however, help the electrical signal penetrate through body tissue. The second waveform 112 can be applied along with the first waveform 108 to an amplitude modulator 114, such as the modulator having the designation On-Semi MC 1496, which is sold by Texas Instruments.

The modulator 114 can be configured to generate a first modulated waveform 116 that is transmitted through a lead 118 to one or more electrodes 120. Four electrodes are illustrated, but the device 100 can include any number of electrodes having any size and shape. The lead 118 can be flexible, as in the illustrated embodiment. The electrodes 120 can be configured to, in turn, apply the first modulated waveform 116 to a first target nerve 122 to stimulate the target nerve 122. The first waveform 108 can be a square wave, and the second waveform 112 can be a sinusoidal signal. The first modulated waveform 116, e.g., the first and second waveforms 108, 112, can define the first electrical signal, e.g., the signal configured to stimulate sympathetic nerves.

The modulator 114 can be configured to generate a second modulated waveform 124 that is transmitted through the lead 118 to one or more of the electrodes 120 to apply the second modulated waveform 124 to a second target nerve (not shown) near the first target nerve 122. The second modulated waveform 124 can define the second electrical signal, e.g., the signal configured to stimulate parasympathetic nerves and/or sensory nerves.

The modulator 114 can be configured to execute a first algorithm to generate the first modulated waveform 116 and can be configured to execute a second algorithm to generate the second modulated waveform 124. The first and second algorithms can be stored in a memory of the modulator 114, e.g., in a memory of the modulator as a microcontroller or other type of processor such as a central processing unit (CPU).

The first and second modulated waveforms 116, 124 each include a modulating signal and a carrier signal in this illustrated embodiment, but a device similar to the device 100 can be configured to similarly generate a single first signal and a single second signal that respectively define the first and second electrical signals. In other words, the first and second electrical signals can each include a single signal, e.g., lack a carrier signal.

The first electrical signal, whether transcutaneously or directly delivered, can be configured in a variety of ways. In an exemplary embodiment, the first electrical signal directly delivered to BAT can have a voltage having an amplitude in a range of about 1 to 20 V, e.g., about 10 V, e.g., about 4 V, about 7 V, etc.; a current having an amplitude in a range of about 2 to 6 mA, e.g., about 3 mA; a pulse width in a range about 10 µs to 1 ms, e.g., about 0.1 ms, about 1 ms, about 0.4 ms, etc.; an activation signal pulse frequency in a range of about 0.1 to 40 Hz, e.g., about 10 Hz or in a range of about 1 to 20 Hz; and a duration of signal train in a range of about 1 second to continuous, e.g., about 30 seconds, etc. Specific parameters for the first electrical signal can be different based on where the first electrical signal is delivered, e.g., based on whether an electrode delivering the first electrical signal is transcutaneously placed or is implanted. In an exemplary embodiment of direct and/or subcutaneous stimulation of myelinated fibers, the first electrical signal can have a current amplitude in a range of about 0.1 to 10 mA and a pulse width in a range of about 50 to 300 µsec. In general, a charge needed to stimulate myelinated fibers is less than a charge needed to stimulate unmyelinated fibers. In an exemplary embodiment of direct and/or subcutaneous stimulation of unmyelinated fibers, the first electrical signal can have a current amplitude greater than and a pulse width at least as high as when applied to myelinated fibers, e.g., the first electrical signal having a current amplitude of greater than 10 mA and a pulse width of at least 300 µsec (e.g., a pulse width in a range of about 300 to 1000 µsec). In an exemplary embodiment of transcutaneous stimulation of myelinated fibers, the first electrical signal can have a current amplitude of at least about 10 mA (e.g., in a range of about 10 to 100 mA) and a pulse width less than about 400 µsec. In general, current amplitudes above 100 mA can be uncomfortable for a patient. In an exemplary embodiment of transcutaneous stimulation of unmyelinated fibers, the first electrical signal can have a current amplitude of at least about 50mA (e.g., in a range of about 50 to 100 mA) and a pulse width in a range of about 400 to 1000 µsec. As will be appreciated by a person skilled in the art, the charge used to stimulate fibers can be adjusted by adjusting the current amplitude and the pulse width to achieve a desired charge. In general, in adjusting the charge, reducing the pulse width for the first electrical signal can be beneficial over increasing the pulse width since very long pulse widths could cause damage and/or discomfort to the patient. A person skilled in the art will appreciate that a specific parameter may not have a precise numerical value but nevertheless be considered to be "about" that specific numerical value due to one or more factors, such as manufacturing tolerances of a device that generates a signal having the specific parameter.

A time between start of signal trains for a noncontinuous electrical signal delivered to BAT can be of any regular, predictable duration, e.g., hourly, daily, coordinated around circadian, ultradian, or other cycles of interest, etc., such as about ten minutes or about ninety minutes, or can be of any irregular, unpredictable duration, e.g., in response to one or more predetermined trigger events. In general, predetermined trigger events include events that are sensed by or otherwise signaled to the device. Non-limiting examples of trigger events include the patient eating, the patient resting (e.g., sleeping), a threshold temperature of the patient (e.g., a temperature in the neuromodulated BAT depot or a core temperature), a directional orientation of the patient (e.g., recumbent as common when sleeping), a change in the patient's weight, a change in the patient's tissue impedance, manual activation by the patient or other human (e.g., via an onboard controller, via a wired or wirelessly connected controller, or upon skin contact), a blood chemistry change in the patient (e.g., a hormonal change), low energy expenditure, menstrual cycles in women, medication intake (e.g., an appetite suppressant such as topiramate, fenfluramine, etc.), an ultradian or other circadian rhythm of the patient, and a manually-generated or automatically-generated signal from a controller in electronic communication, wired and/or wireless, with the device. In one embodiment, the patient eating can be determined through a detection of heart rate variability, as discussed in more detail in U.S. Pat. No. 8,696,616 filed on Dec. 29, 2010 entitled "Obesity Therapy And Heart Rate Variability" and U.S. Pat. Pub. No. 2012/0172783 filed on Dec. 29, 2010 and entitled "Obesity Therapy And Heart Rate Variability," which are hereby incorporated by reference in their entireties.

A length of time for a continuously delivered BAT signal can vary. To more accurately simulate a weight loss surgery that has a continuous or chronic effect on a patient for an extended period of time, the first electrical signal can be continuously or chronically delivered for an extended, and preferably predetermined, amount of time. In an exemplary embodiment, the predetermined amount of time can be at least one day, e.g., in a range of one day to at least four weeks, at least one week, at least four weeks, etc. Various exemplary embodiments of the first electrical signal that can be delivered to stimulate BAT are further described in, for example, previously mentioned U.S. Pat. Pub. No. 2011/0270360 entitled "Methods And Devices For Activating Brown Adipose Tissue Using Electrical Energy" filed Dec. 29, 2010.

The second electrical signal, whether transcutaneously or directly delivered, can be configured in a variety of ways. In an exemplary embodiment, the second electrical signal can be different than the first electrical signal in one or more ways, e.g., have a different voltage, a different current, a different amplitude, a different pulse width, a different polarity, etc. In this way, the first electrical signal can be targeted to a first nerve type, e.g., sympathetic nerves, by having a first configuration, and the second electrical signal can be targeted to a second, different nerve type, e.g., parasympathetic nerves and/or sensory nerves, by having a second configuration that is different than the first configuration.

The second electrical signal being different than the first electrical signal can allow the second electrical signal to target parasympathetic nerves using fiber diameter selectivity. In other words, the second electrical signal can be configured to activate nerve fibers having a first diameter without activating nerve fibers having diameters different than the first diameter. As discussed above, sympathetic nerves include postganglionic unmyelinated, small diameter fibers, while parasympathetic nerves include preganglionic myelinated, larger diameter fibers. The second electrical signal can thus be configured to target and activate the preganglionic myelinated, larger diameter fibers without activating the postganglionic unmyelinated, small diameter fibers. The energy required to activate the postganglionic unmyelinated, small diameter fibers (e.g., the sympathetic nerves) is greater than the energy required to activate the preganglionic myelinated, larger diameter fibers (e.g., the parasympathetic nerves). The relative energies of the first and second electrical signals can allow the lower energy second electrical signal to suppress the parasympathetic fibers without activating the sympathetic nerves. After suppression of the parasympathetic fibers, the higher energy first electrical signal can activate the sympathetic fibers without activating the suppressed parasympathetic nerves.

Signal characteristics of the first and second electrical signals can be controlled to facilitate the targeting of nerves using fiber diameter selectivity. Threshold differences between the first and second electrical signals can be controlled by varying signal characteristics of the first and second electrical signals, such as pulse width and delay between first and second pulses of a biphasic waveform.

In an exemplary embodiment, the second electrical signal can be different than the first electrical signal by having less energy than the first electrical signal. For example, a current of the first electrical signal can be greater than a current of the second electrical signal. Sympathetic nerves are postganglionic, and postganglionic fibers are unmyelinated and generally have a small diameter. Conversely, parasympathetic nerves and sensory nerves are pre-ganglionic and are myelinated and generally have a larger diameter than sympathetic nerves. The second electrical signal having a current less than the first electrical signal's current can facilitate the second electrical signal's suppression of the myelinated nerves before the first electrical signal begins to be applied and can facilitate the second electrical signal's suppression of the myelinated nerves while the first electrical signal also being applied stimulates the unmyelinated nerves. The second electrical signal can be applied before the first electrical signal is applied, thereby preventing new action potential formation at the parasympathetic nerves such that the first electrical signal subsequently applied cannot activate the parasympathetic nerves. In an exemplary embodiment, the first electrical signal's current can be in a range of ten to one hundred times greater than a current of the second electrical signal, which can help ensure that the first electrical signal targets the first nerve type and the second electrical signal targets the second nerve type. For example, the second electrical signal can have a current in a range of about 0.1 mA to 5 mA, and the first electrical signal can have a current in a range of ten to one hundred times greater than the second electrical signal. For another example, the second electrical signal can have a pulse width that is equal to or less than a pulse width of the first electrical signal, such as by the second electrical signal having a pulse width in a range of about 10 μs to 400 μs, and the first electrical signal having a pulse width in a range of about 400 μs to 1000 μs. In an exemplary embodiment, the second electrical signal has a pulse width that is less than a pulse width of the first electrical signal.

For another example of the second electrical signal having less energy than the first electrical signal, the second electrical signal can include a hyperpolarizing lower energy pulse (e.g., an anodic signal) as compared to the first electrical signal. The hyperpolarizing lower energy pulse of the second electrical signal can facilitate inhibition of the second nerve type while the first electrical signal stimulates the first nerve type. The hyperpolarizing lower energy pulse of the second electrical signal can be configured to inactivate sodium channels, thereby preventing new action potential formation. The second electrical signal including the hyperpolarizing lower energy pulse can be applied to BAT before the first electrical signal is applied to the BAT, thereby preventing new action potential formation at the parasympathetic nerves such that the first electrical signal subsequently applied to the BAT cannot activate the parasympathetic nerves. The first and second electrical signals can be alternately applied, thereby helping to ensure that the parasympathetic nerves having the hyperpolarizing lower energy pulse applied thereto are not activated in response to application of the first electrical signal.

For another example of the second electrical signal having less energy than the first electrical signal, the second electrical signal can include a depolarizing lower energy pulse (e.g., a cathodic stimulus) as compared to the first electrical signal. The depolarizing lower energy pulse of the second electrical signal can facilitate inhibition of the second nerve type while the first electrical signal stimulates the first nerve type. The depolarizing lower energy pulse of the second electrical signal can be configured to depolarize parasympathetic nerves without activating the parasympathetic nerves (e.g., be lower than that needed to cause activation of the parasympathetic nervous system) such that no new action potential can be elicited from the parasympathetic nerves. The second electrical signal including the depolarizing lower energy pulse can be applied to BAT before the first electrical signal is applied to the BAT, thereby depolarizing the parasympathetic nerves such that the first electrical signal subsequently applied to the BAT cannot activate the parasympathetic nerves. The first and second electrical signals can be alternately applied, thereby helping to ensure that the parasympathetic nerves having the depolarizing lower energy pulse applied thereto are not activated in response to application of the first electrical signal.

In another exemplary embodiment of activating a first nerve type innervating BAT and inhibiting a second nerve type innervating BAT, the BAT can be neuromodulated using an electrical signal and a chemical. For example, the electrical signal can target the first nerve type, and the chemical can target the second nerve type. For another example, the chemical can target the first nerve type, and the electrical signal can target the second nerve type.

In one exemplary embodiment, the electrical signal can target the first nerve type, and a chemical in the form of an anticholinergic agent (e.g., atropine, etc.) can target the second nerve type. An anticholinergic agent is, generally, a substance that blocks the neurotransmitter acetylcholine in the central and the peripheral nervous system, which as discussed above can help suppress parasympathetic activity and thereby improve the effectiveness of the BAT neuromodulation. Anticholinergics are a class of medications that inhibit parasympathetic nerve impulses by selectively blocking the binding of the neurotransmitter acetylcholine to its receptor in nerve cells. The Anticholinergics are divided into three categories in accordance with their specific targets in the central and/or peripheral nervous system: antimuscarinic agents, ganglionic blockers, and neuromuscular blockers.

In another exemplary embodiment, the electrical signal can target the first nerve type, and a chemical in the form of a depolarization agent can target the second nerve type. Thus, similar to that discussed above regarding the second electrical signal including a depolarizing lower energy pulse, the depolarization agent can facilitate inhibition of the second nerve type while the electrical signal stimulates the first nerve type.

In still another exemplary embodiment, the electrical signal can target the first nerve type, and a chemical in the form of a hyperpolarization agent can target the second nerve type. Thus, similar to that discussed above regarding the second electrical signal including a hyperpolarizing lower energy pulse, the hyperpolarization agent can facilitate inhibition of the second nerve type while the electrical signal stimulates the first nerve type.

In yet another exemplary embodiment, the electrical signal can target the first nerve type, and a chemical can be configured to target the second nerve type by targeting a temperature-sensitive nature of the second nerve type. In other words, the second nerve type can include sensory nerves sensitive to temperature, and the chemical can be configured to suppress the sensory nerves by affecting a temperature of the sensory nerves.

In another exemplary embodiment of activating a first nerve type innervating BAT and inhibiting a second nerve type innervating BAT, the BAT can be neuromodulated using a first chemical and a second chemical. The first chemical can be configured to stimulate the sympathetic nerves, and the second chemical can be configured to inhibit the other nerve type, e.g., to inhibit parasympathetic nerves and/or sensory nerves. In an exemplary embodiment, the second chemical can be different than the first chemical, thereby facilitating the targeting of different nerve types by the first and second chemicals.

In another exemplary embodiment of activating a first nerve type innervating BAT and inhibiting a second nerve type innervating BAT, the first nerve type can be stimulated using at least one of an electrical signal, a chemical, cooling, and a light, and the second nerve type can be stimulated using at least one of a different electrical signal and a different chemical.

The devices discussed herein can be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces, and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

Preferably, the invention described herein will be processed before use. First, a new or used instrument is obtained and if necessary cleaned. The instrument can then be sterilized. In one sterilization technique, the instrument is placed in a closed and sealed container, such as a plastic or TYVEK bag. The container and instrument are then placed in a field of radiation that can penetrate the container, such as gamma radiation, x-rays, or high-energy electrons. The radiation kills bacteria on the instrument and in the container. The sterilized instrument can then be stored in the sterile container. The sealed container keeps the instrument sterile until it is opened in the medical facility.

It is preferred that device is sterilized. This can be done by any number of ways known to those skilled in the art including beta or gamma radiation, ethylene oxide, steam, and a liquid bath (e.g., cold soak). An exemplary embodiment of sterilizing a device including internal circuitry is described in more detail in U.S. Pat. Pub. No. 2009/0202387 filed Feb. 8, 2008 and entitled "System And Method Of Sterilizing An Implantable Medical Device." It is preferred that device, if implanted, is hermetically sealed. This can be done by any number of ways known to those skilled in the art.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A medical method, comprising:
applying a first neuromodulator to a depot of brown adipose tissue (BAT), the application of the first neuromodulator causing activation of a first nerve type in the BAT so as to increase energy expenditure of the BAT, wherein applying the first neuromodulator comprises at least one of applying an electrical signal to the depot of BAT, delivering a chemical to the depot of BAT, cooling the depot of BAT, and applying a light to the depot of BAT; and applying a second neuromodulator to the depot of BAT simultaneously with the application of the first neuromodulator, the application of the second neuromodulator inhibiting a second nerve type in the BAT that is different from the first nerve type, wherein applying the second neuromodulator comprises at least one of applying a different electrical signal to the depot of BAT, delivering a different chemical to the depot of BAT, cooling the depot of BAT, and applying a different light to the depot of BAT;

wherein the application of the second neuromodulator starts before the application of the first neuromodulator begins so as to start inhibiting the second nerve type before the first nerve type is activated; and wherein the application of the first neuromodulator is configured to cause activation of the second nerve type, and the application of the second neuromodulator starts before the application of the first neuromodulator begins so as to prevent the second nerve type from being activated by the application of the first neuromodulator.

2. The method of claim 1, wherein the first nerve type includes sympathetic nerves, and the second nerve type includes parasympathetic nerves.

3. The method of claim 1, wherein the first nerve type includes sympathetic nerves, and the second nerve type includes sensory nerves.

4. The method of claim 1, wherein applying the first neuromodulator comprises applying a first electrical signal to the depot of BAT, and applying the second neuromodulator comprises applying a second electrical signal to the depot of BAT that is different from the first electrical signal.

5. The method of claim 1, wherein applying one of the first and second neuromodulators comprises applying an electrical signal to the depot of BAT, and applying the other of the first and second neuromodulators comprises delivering a chemical to the depot of BAT.

6. The method of claim 1, wherein applying the first neuromodulator comprises delivering a first chemical to the depot of BAT, and applying the second neuromodulator comprises delivering a second chemical to the depot of BAT that is different from the first chemical.

7. A medical method, comprising:
neuromodulating a sympathetic nervous system of a patient proximate to a depot of brown adipose tissue (BAT) of a patient so as to activate the BAT and increase energy expenditure of the BAT, wherein neuromodulating the sympathetic nervous system comprises applying a first electrical signal to the patient; and simultaneously with the neuromodulating of the sympathetic nervous system, suppressing a parasympathetic nervous system of the patient proximate to the depot of brown adipose tissue, wherein suppressing the parasympathetic nervous system comprises applying a second electrical signal to the patient, the second electrical signal having less energy than the first electrical signal by as compared to the first electrical signal, or by including a depolarizing lower energy pulse as compared to the first electrical signal.

8. The method of claim 7, wherein neuromodulating the sympathetic nervous system activates sympathetic nerves innervating the BAT, and suppressing the parasympathetic nervous system suppresses parasympathetic nerves innervating the BAT, each of the parasympathetic nerves having a larger diameter than each of the sympathetic nerves.

9. The method of claim 7, wherein the suppression of the parasympathetic nervous system begins before the neuromodulation of the sympathetic nervous system so as to start suppressing the parasympathetic nervous system before the sympathetic nervous system is neuromodulated.

10. The method of claim 7, wherein the second electrical signal has less energy than the first electrical signal by having less current than the first electrical signal, and a current of the first electrical signal is in a range of ten to one hundred times greater than a current of the second electrical signal.

11. The method of claim 4, further comprising selecting the first and second electrical signals based on a diameter of nerve fibers of the first nerve type and a diameter of nerve fibers of the second nerve type.

12. The method of claim 4, wherein the second electrical signal has less energy than the first electrical signal.

13. The method of claim 12, wherein the second electrical signal has less energy than the first electrical signal by having less current than the first electrical signal, by including a hyperpolarizing lower energy pulse as compared to the first electrical signal, or by including a depolarizing lower energy pulse as compared to the first electrical signal.

14. A medical method, comprising:
neuromodulating a sympathetic nervous system of a patient proximate to a depot of brown adipose tissue (BAT) of a patient by delivering a first stimulation to the BAT so as to activate the BAT and increase energy expenditure of the BAT; and simultaneously with the neuromodulating of the sympathetic nervous system, suppressing a parasympathetic nervous system of the patient proximate to the depot of brown adipose tissue by delivering a second stimulation to the BAT;

wherein the delivery of the second stimulation starts before the delivery of the first stimulation such that suppression of the parasympathetic nervous system starts before the neuromodulation of the sympathetic nervous system, and wherein the delivery of the first stimulation is configured to cause activation of the parasympathetic nervous system, and the delivery of the second stimulation starts before the delivery of the first stimulation so as to prevent the parasympathetic nervous system from being activated by the delivery of the first stimulation.

15. The method of claim 14, wherein neuromodulating the sympathetic nervous system activates sympathetic nerves innervating the BAT, and suppressing the parasympathetic nervous system suppresses parasympathetic nerves innervating the BAT, each of the parasympathetic nerves having a larger diameter than each of the sympathetic nerves.

16. The method of claim 14, wherein neuromodulating the sympathetic nervous system comprises delivering a first electrical signal to the patient, and suppressing the parasympathetic nervous system comprises delivering a second electrical signal to the patient that is different than the first electrical signal.

17. The method of claim 16, wherein a current of the first electrical signal is in a range of ten to one hundred times greater than a current of the second electrical signal.

18. The method of claim 16, wherein the second electrical signal comprises one of a hyperpolarizing lower energy pulse as compared to the first electrical signal, and a depolarizing lower energy pulse as compared to the first electrical signal.

19. The method of claim 14, wherein neuromodulating the sympathetic nervous system comprises delivering a first electrical signal to the patient, and suppressing the parasympathetic nervous system comprises delivering a chemical to the patient.

20. The method of claim 14, wherein neuromodulating the sympathetic nervous system comprises delivering a first chemical to the patient, and suppressing the parasympathetic nervous system comprises one of delivering a second chemical to the patient that is different than the first chemical and delivering an electrical signal to the patient.

21. The method of claim 14, wherein neuromodulating the sympathetic nervous system comprises at least one of delivering an electrical signal to the patient, delivering a chemical to the patient, cooling the patient, and delivering a light to the patient.

* * * * *